United States Patent
Vojdani

(10) Patent No.: US 7,390,626 B2
(45) Date of Patent: Jun. 24, 2008

(54) METHODS AND KIT FOR DIAGNOSING TICK BORNE ILLNESSES

(75) Inventor: Aristo Vojdani, Los Angeles, CA (US)

(73) Assignee: Immunosciences Lab., Inc., Beverly Hills, CA (US)

(*) Notice: Subject to any disclaimer, the term of this patent is extended or adjusted under 35 U.S.C. 154(b) by 420 days.

(21) Appl. No.: 11/066,399

(22) Filed: Feb. 25, 2005

(65) Prior Publication Data

US 2006/0194267 A1 Aug. 31, 2006

(51) Int. Cl.
*G01N 33/53* (2006.01)
*G01N 33/554* (2006.01)
*G01N 33/567* (2006.01)
*G01N 33/569* (2006.01)
*A61K 39/018* (2006.01)
*C12Q 1/68* (2006.01)

(52) U.S. Cl. .................. 435/7.1; 424/150.1; 424/151.1; 424/234.1; 424/270.1; 435/6; 435/7.2; 435/7.32; 435/7.8; 435/7.92; 435/7.93; 435/7.94; 435/7.95; 435/29; 435/174; 435/331; 435/332; 435/340; 435/342; 436/164; 436/174; 436/501; 436/517; 436/536; 436/538; 436/540

(58) Field of Classification Search .............. 424/151.1, 424/150.1, 234.1, 270.1; 435/4, 7.1, 7.2, 435/7.22, 7.91, 7.92, 7.95, 283.1, 305.1, 435/6, 7.32, 7.93, 7.94, 29, 174, 331, 332, 435/340, 342; 436/165, 172, 501, 513, 536, 436/164, 174, 517, 538, 540
See application file for complete search history.

(56) References Cited

FOREIGN PATENT DOCUMENTS

| WO | WO 01/20325 | * | 3/2001 |
| WO | WO 01/20325 A | | 3/2001 |

OTHER PUBLICATIONS

Magnarelli et al. 2000. J. Clin. Microbio. vol. 38(5): 1735-1739.*
Magnarelli et al. 1998. vol. 36(10): 2823-2827.*
E. Asbrink, et al., "Successful Cultivation of Spirochetes From Skin Lesions of Patients with Erythema Chronicum Migrans Afzelius and Acrodermatitis Chronica Atrophicans," *Acta Path. Microbiol. Immunol. Scand.*, Sect. B, 93: 161-163, 1985.
L.R. Brunet, et al., "Short Report: Density of Lyme Disease Spirochetes Within Deer Ticks Collected From Zoonotic Sites," *Am J. Trop. Med. Hyg.*, 53(3), 1995, pp. 300-302.
J.D. Cooper, et al., "Lyme Disease: Difficulties in Diagnosis," *Infections in Medicine*, vol. 11, No. 7, Jul. 1994, pp. 479 and 509-514.

(Continued)

*Primary Examiner*—Mark Navarro
*Assistant Examiner*—JaNa Hines
(74) *Attorney, Agent, or Firm*—Knobbe, Martens, Olson & Bear LLP

(57) ABSTRACT

ELISA, Western Blot, and a peptide-based ELISA were applied to clinical specimens from patients with clinical symptoms of tick borne diseases, including Lyme disease. Peptides from different components of *Borrelia* during different cycles, including peptides from outer surface protein, leukocyte function associated antigens, immunodominant antigens, variable major proteins, and peptides from decorin-binding proteins of Borrelial subspecies (*B. sensu stricto. B. afzelii, B. garinii*) were used. Antibodies against specific peptides from *Babesia* and *Ehrlichia* were also measured.

11 Claims, 29 Drawing Sheets

OTHER PUBLICATIONS

J.E. Craft, et al., "Antibody Response in Lyme Disease: Evaluation of Diagnostic Tests," *The Journal of Infectious Diseases*, vol. 149, No. 5, May 1984, pp. 789-795.

F. Dressler, et al., "Western Blotting in the Serodiagnosis of Lyme Disease," *Journal of Infectious Diseases*, 1993; 167:392-400.

S. M. Engstrom, et al., "Immunoblot Interpretation Criteria for Serodiagosis of Early Lyme Disease," *Journal of Clinical Microbiology*, Feb. 1995, pp. 419-427.

R. D. Gilmore, Jr., et al., "Molecular Characterization of a 35-Kilodalton Protein of Borrelia burgdorferi, an Antigen of Diagnostic Importance in Early Lyme Disease," *Journal of Clinical Microbiology*, Jan. 1997, pp. 86-91.

J. L. Goodman, "Ch. 16. Nucleic Acid Detection of *Borrelia burgdorferi* Infection," pp. 127-135. In P.K. Coyle (ed) Lyme Disease. Mosby-Year Book Inc., St. Louis, MO 1993.

J.L. Goodman, et al., "Bloodstream Invasion in Early Lyme Disease: Results From a Prospective, Controlled, Blinded Study Using the Polymerase Chain Reaction," *The American Journal of Medicine*, vol. 99, Jul. 1995, pp. 6-12.

J.L. Goodman, et al., "Molecular Detection of Persistent *Borrelia burgdorferi* in the Urine of Patients with Active Lyme Disease," *Infection and Immunity*, Jan. 1991, pp. 269-278.

C.W. Hedberg, et al., "An Interlaboratory Study of Antibody to Borrelia burgdorferi," *The Journal of Infectious Diseases*, vol. 155, No. 6, Jun. 1987, pp. 1325-1327.

C.W. Hedberg, et al., "Serologic Tests for Antibody to *Borrelia burgdorferi*. Another Pandora's Box for Medicine?" *Arch Intern Med.*, vol. 150, Apr. 1990, pp. 732-734.

J.M. Jones, "Serodiagnosis of Lyme Disease," *Annals of Internal Medicine*, vol. 114, No. 12, Jun. 15, 1991, p. 1064.

F.S. Kantor, "Disarming Lyme Disease," *Scientific American*, Sep. 1994, pp. 34-39.

M. Karlsson, et al., "Cultivation and Characterization of Spirochetes from Cerebrospinal Fluid of Patients with Lyme Borreliosis," *Journal of Clinical Microbiology*, Mar. 1990, pp. 473-479.

R. S. Lane, et al., "Interlaboratory and Intralaboratory Comparisons of Indirect Immunofluorescence Assays for Serodiagnosis of Lyme Disease," *Journal of Clinical Microbiology*, Aug. 1990, pp. 1774-1779.

S.W. Luger, et al., "Serologic Tests of Lyme Disease. Interlaboratory Variability" *Arch Intern Med.*, vol. 150, Apr. 1990, pp. 761-763.

B.S. Schwartz, et al., "Antibody Testing in Lyme Disease. A comparison of Results in Four Laboratories," *JAMA*, Dec. 22/29, 1989, vol. 262, No. 24, pp. 3431-3434.

G. Stanek, et al., "European Lyme Borreliosis," pp. 274-282. In "Lyme Disease and Related Disorders", vol. 539, J.L. Benach and E.M. Bosler (eds.) The New York Academy of Sciences, 1988.

A.C. Steere, "Lyme Disease," *The New England Journal of Medicine*, Aug. 31, 1989, pp. 586-596.

A.C. Steere, et al., "Chronic Lyme Arthritis. Clinical and Immunogenetic Differentiation from Rheumatoid Arthritis," *Annals of Internal Medicine*, 90:896-901, 1979, pp. 896-901.

A.C. Steere, et al., "The Spirochetal Etiology of Lyme Disease," *N Engl J Med.*, 1983; 308: 733-40.

A.C. Steere, et al., "Lyme Arthritis. An Epidemic of Oligoarticular Arthritis in Children and Adults in Three Connecticut Communities," *Arthritis and Rheumatism*, vol. 20, No. 1 Jan.-Feb. 1977, pp. 7-17.

A.C. Steere, et al., "The Overdiagnosis of Lyme Disease," *JAMA*, Apr. 14, 1993, vol. 269, No. 14, pp. 1812-1816.

Magnarelli et al. *Journal of Clinical Microbiology*. 33(11):3054-3057 (1995).

Vojdani et al. *Faseb Journal, Fed. of American Soc. for Experimental Biology*. 19(4; Supp. Part 1):A965 (2005).

Bachmaier et al. *Nature Medicine*. 6(8):841-842 (2000).

Gomes-Solecki et al. *BMC Musculoskeletal Disorders*. 3(1):1471-2474 (2002).

Liang et al. *Infection and Immunity*. 67(12):6702-6706 (1999).

Norimine et al. *Immunogenetics*. 57(10):750-762 (2005).

Lahmers et al. *Journal of Leukocyte Biology*. 77(2):199-208 (2005).

* cited by examiner

| | | |
|---|---|---|
| A | ○○ | Unrelated peptide (Treponema palidum) |
| B | ○○ | Coated with B. burgdorferi lysate |
| C | ○○ | Coated with outer surface protein-A + outer surface protein-C |
| D | ○○ | Coated with outer surface protein-E |
| E | ○○ | Coated with leukocyte function associated antigen |
| F | ○○ | Coated with immunodominant protein of invariable region |
| G | ○○ | Coated with variable major protein |
| H | ○○ | Coated with Decorin binding protein of B. b. sensu stricto |
| I | ○○ | Coated with Decorin binding protein of B. garinii |
| J | ○○ | Coated with Decorin binding protein of B. afzelii |
| K | ○○ | Coated with Babesia peptide |
| L | ○○ | Coated with Ehrlichial peptide |

FIG. 1

| Wells are coated with: | Negative Control | | Positive Control | | Patient's Sample | |
|---|---|---|---|---|---|---|
| Unrelated peptide | 0.13 | 0.14 | 0.35 | 0.31 | 0.87 | 0.82 |
| B. burgdorferi lysate | 0.15 | 0.18 | 2.70 | 2.85 | 1.30 | 1.41 |
| Outer surface protein-A + outer surface protein-C | 0.16 | 0.19 | 0.75 | 0.83 | 1.15 | 1.20 |
| Outer surface protein-E | 0.18 | 0.22 | 0.29 | 0.32 | 0.29 | 0.31 |
| Leukocyte function associated antigen | 0.17 | 0.15 | 1.75 | 1.82 | 0.34 | 0.33 |
| Immunodominant protein of invariable region | 0.20 | 0.18 | 2.30 | 2.45 | 0.76 | 0.82 |
| Variable major protein | 0.17 | 0.12 | 0.64 | 0.58 | 0.39 | 0.42 |
| Decorin binding protein of B.b. sensu stricto | 0.14 | 0.16 | 2.38 | 2.26 | 1.45 | 1.53 |
| Decorin binding protein of B. garinii | 0.18 | 0.14 | 0.26 | 0.34 | 0.38 | 0.41 |
| Decorin binding protein of B. afzelii | 0.19 | 0.23 | 0.19 | 0.26 | 0.55 | 0.64 |
| Babesia peptide | 0.20 | 0.16 | 0.22 | 0.28 | 1.61 | 1.49 |
| Ehrlichia peptide | 0.15 | 0.13 | 0.46 | 0.51 | 0.32 | 0.34 |

FIG. 6

| Wells are coated with: | Negative Control | | Positive Control | | Patient's Sample | |
|---|---|---|---|---|---|---|
| Unrelated peptide | 0.21 | 0.18 | 0.27 | 0.21 | 0.34 | 0.37 |
| B. burgdorferi lysate | 0.25 | 0.28 | 1.65 | 1.82 | 0.62 | 0.57 |
| Outer surface protein-A + outer surface protein-C | 0.17 | 0.15 | 0.24 | 0.33 | 0.55 | 0.59 |
| Outer surface protein-E | 0.19 | 0.21 | 0.18 | 0.23 | 0.29 | 0.32 |
| Leukocyte function associated antigen | 0.26 | 0.22 | 0.29 | 0.35 | 0.27 | 0.33 |
| Immunodominant protein of invariable region | 0.18 | 0.17 | 1.38 | 1.27 | 0.31 | 0.30 |
| Variable major protein | 0.13 | 0.19 | 0.42 | 0.51 | 0.32 | 0.27 |
| Decorin binding protein of B.b. sensu stricto | 0.24 | 0.31 | 1.37 | 1.28 | 0.68 | 0.65 |
| Decorin binding protein of B. garinii | 0.26 | 0.20 | 0.44 | 0.39 | 0.35 | 0.31 |
| Decorin binding protein of B. afzelii | 0.11 | 0.19 | 0.28 | 0.32 | 0.38 | 0.33 |
| Babesia peptide | 0.17 | 0.23 | 0.37 | 0.40 | 0.98 | 0.95 |
| Ehrlichia peptide | 0.24 | 0.18 | 0.57 | 0.63 | 0.28 | 0.32 |

FIG. 7

| Wells are coated with: | Negative Control | | Positive Control | | Patient's Sample | |
|---|---|---|---|---|---|---|
| Unrelated peptide | 0.15 | 0.18 | 0.39 | 0.35 | 0.51 | 0.55 |
| B. burgdorferi lysate | 0.17 | 0.19 | 2.56 | 2.60 | 1.90 | 2.10 |
| Outer surface protein-A + outer surface protein-C | 0.13 | 0.14 | 0.78 | 0.71 | 1.00 | 0.98 |
| Outer surface protein-E | 0.15 | 0.17 | 0.25 | 0.31 | 0.91 | 0.85 |
| Leukocyte function associated antigen | 0.16 | 0.21 | 1.69 | 1.77 | 0.61 | 0.63 |
| Immunodominant protein of invariable region | 0.18 | 0.22 | 2.20 | 2.43 | 1.45 | 1.39 |
| Variable major protein | 0.15 | 0.19 | 0.55 | 0.61 | 0.51 | 0.58 |
| Decorin binding protein of B.b. sensu stricto | 0.17 | 0.23 | 2.59 | 2.45 | 1.71 | 1.65 |
| Decorin binding protein of B. garinii | 0.22 | 0.20 | 0.25 | 0.33 | 1.37 | 1.39 |
| Decorin binding protein of B. afzelii | 0.14 | 0.17 | 0.21 | 0.29 | 0.12 | 1.15 |
| Babesia peptide | 0.19 | 0.15 | 0.17 | 0.18 | 1.26 | 1.22 |
| Ehrlichia peptide | 0.22 | 0.19 | 0.53 | 0.55 | 0.38 | 0.41 |

*FIG. 10*

| Wells are coated with: | Negative Control | | Positive Control | | Patient's Sample | |
|---|---|---|---|---|---|---|
| Unrelated peptide | 0.24 | 0.21 | 0.25 | 0.28 | 0.61 | 0.67 |
| B. burgdorferi lysate | 0.17 | 0.22 | 1.85 | 1.69 | 1.53 | 1.45 |
| Outer surface protein-A + outer surface protein-C | 0.15 | 0.19 | 0.25 | 0.31 | 0.38 | 0.31 |
| Outer surface protein-E | 0.21 | 0.26 | 0.26 | 0.21 | 0.33 | 0.31 |
| Leukocyte function associated antigen | 0.24 | 0.28 | 0.28 | 0.31 | 0.91 | 0.78 |
| Immunodominant protein of invariable region | 0.14 | 0.19 | 1.45 | 1.36 | 1.41 | 1.35 |
| Variable major protein | 0.18 | 0.18 | 0.51 | 0.48 | 0.31 | 0.29 |
| Decorin binding protein of B.b. sensu stricto | 0.26 | 0.21 | 1.36 | 1.44 | 1.76 | 1.81 |
| Decorin binding protein of B. garinii | 0.19 | 0.20 | 0.49 | 0.41 | 1.09 | 1.06 |
| Decorin binding protein of B. afzelii | 0.17 | 0.18 | 0.26 | 0.29 | 0.69 | 0.58 |
| Babesia peptide | 0.25 | 0.23 | 0.38 | 0.43 | 1.41 | 1.27 |
| Ehrlichia peptide | 0.21 | 0.20 | 0.65 | 0.61 | 0.48 | 0.56 |

FIG. 11

| Wells are coated with: | Negative Control | | Positive Control | | Patient's Sample | |
|---|---|---|---|---|---|---|
| Unrelated peptide | 0.17 | 0.21 | 0.36 | 0.41 | 0.65 | 0.78 |
| B. burgdorferi lysate | 0.18 | 0.27 | 2.38 | 2.54 | 1.25 | 1.13 |
| Outer surface protein-A + outer surface protein-C | 0.21 | 0.16 | 0.81 | 0.75 | 1.92 | 1.74 |
| Outer surface protein-E | 0.22 | 0.20 | 0.17 | 0.28 | 0.30 | 0.25 |
| Leukocyte function associated antigen | 0.14 | 0.18 | 1.59 | 1.67 | 0.78 | 0.89 |
| Immunodominant protein of invariable region | 0.19 | 0.13 | 2.10 | 1.98 | 0.39 | 0.42 |
| Variable major protein | 0.22 | 0.28 | 0.45 | 0.62 | 0.85 | 0.81 |
| Decorin binding protein of B.b. sensu stricto | 0.16 | 0.21 | 2.44 | 2.32 | 0.31 | 0.32 |
| Decorin binding protein of B. garinii | 0.24 | 0.29 | 0.17 | 0.25 | 1.52 | 1.74 |
| Decorin binding protein of B. afzelii | 0.23 | 0.17 | 0.33 | 0.29 | 0.25 | 0.32 |
| Babesia peptide | 0.13 | 0.16 | 0.13 | 0.24 | 0.76 | 0.83 |
| Ehrlichia peptide | 0.17 | 0.24 | 0.45 | 0.62 | 0.31 | 0.33 |

FIG. 14

| Wells are coated with: | Negative Control | | Positive Control | | Patient's Sample | |
|---|---|---|---|---|---|---|
| Unrelated peptide | 0.31 | 0.25 | 0.35 | 0.39 | 0.95 | 1.11 |
| B. burgdorferi lysate | 0.24 | 0.21 | 1.96 | 1.76 | 1.17 | 1.12 |
| Outer surface protein-A + outer surface protein-C | 0.18 | 0.22 | 0.34 | 0.36 | 1.38 | 1.29 |
| Outer surface protein-E | 0.16 | 0.19 | 0.29 | 0.18 | 0.16 | 0.72 |
| Leukocyte function associated antigen | 0.25 | 0.21 | 0.26 | 0.35 | 1.28 | 1.45 |
| Immunodominant protein of invariable region | 0.27 | 0.23 | 1.57 | 1.43 | 1.31 | 1.48 |
| Variable major protein | 0.14 | 0.16 | 0.62 | 0.57 | 1.39 | 1.52 |
| Decorin binding protein of B.b. sensu stricto | 0.28 | 0.31 | 1.49 | 1.53 | 0.61 | 0.68 |
| Decorin binding protein of B. garinii | 0.18 | 0.25 | 0.54 | 0.45 | 2.59 | 2.74 |
| Decorin binding protein of B. afzelii | 0.24 | 0.26 | 0.36 | 0.31 | 0.60 | 0.73 |
| Babesia peptide | 0.21 | 0.28 | 0.41 | 0.47 | 2.35 | 2.54 |
| Ehrlichia peptide | 0.26 | 0.18 | 0.71 | 0.52 | 0.55 | 0.63 |

FIG. 15

| Wells are coated with: | Negative Control | | Positive Control | | Patient's Sample | |
|---|---|---|---|---|---|---|
| Unrelated peptide | 0.15 | 0.18 | 0.41 | 0.44 | 0.31 | 0.30 |
| B. burgdorferi lysate | 0.13 | 0.17 | 2.61 | 2.74 | 0.70 | 0.66 |
| Outer surface protein-A + outer surface protein-C | 0.21 | 0.27 | 0.59 | 0.67 | 0.81 | 0.75 |
| Outer surface protein-E | 0.29 | 0.25 | 0.18 | 0.29 | 0.28 | 0.31 |
| Leukocyte function associated antigen | 0.17 | 0.22 | 1.92 | 1.74 | 0.32 | 0.30 |
| Immunodominant protein of invariable region | 0.17 | 0.15 | 2.11 | 2.32 | 0.31 | 0.30 |
| Variable major protein | 0.20 | 0.18 | 0.72 | 0.54 | 0.30 | 0.25 |
| Decorin binding protein of B.b. sensu stricto | 0.13 | 0.16 | 2.18 | 2.37 | 0.28 | 0.32 |
| Decorin binding protein of B. garinii | 0.18 | 0.15 | 0.16 | 0.25 | 0.27 | 0.25 |
| Decorin binding protein of B. afzelii | 0.19 | 0.22 | 0.21 | 0.24 | 0.26 | 0.31 |
| Babesia peptide | 0.21 | 0.17 | 0.20 | 0.27 | 0.27 | 0.22 |
| Ehrlichia peptide | 0.24 | 0.28 | 0.53 | 0.48 | 0.31 | 0.28 |

FIG. 18

| Wells are coated with: | Negative Control | | Positive Control | | Patient's Sample | |
|---|---|---|---|---|---|---|
| Unrelated peptide | 0.18 | 0.20 | 0.29 | 0.25 | 0.25 | 0.31 |
| B. burgdorferi lysate | 0.23 | 0.25 | 1.75 | 1.78 | 0.32 | 0.28 |
| Outer surface protein-A + outer surface protein-C | 0.25 | 0.28 | 0.21 | 0.32 | 0.21 | 0.26 |
| Outer surface protein-E | 0.17 | 0.15 | 0.25 | 0.19 | 0.25 | 0.29 |
| Leukocyte function associated antigen | 0.19 | 0.21 | 0.26 | 0.21 | 0.18 | 0.26 |
| Immunodominant protein of invariable region | 0.11 | 0.17 | 1.46 | 1.53 | 0.29 | 0.21 |
| Variable major protein | 0.25 | 0.22 | 0.38 | 0.45 | 0.27 | 0.25 |
| Decorin binding protein of B.b. sensu stricto | 0.13 | 0.19 | 1.43 | 1.32 | 0.17 | 0.21 |
| Decorin binding protein of B. garinii | 0.26 | 0.32 | 0.37 | 0.48 | 0.15 | 0.19 |
| Decorin binding protein of B. afzelii | 0.26 | 0.21 | 0.31 | 0.39 | 0.28 | 0.31 |
| Babesia peptide | 0.14 | 0.19 | 0.32 | 0.41 | 0.27 | 0.25 |
| Ehrlichia peptide | 0.23 | 0.20 | 0.47 | 0.62 | 0.28 | 0.26 |

FIG. 19

| Wells are coated with: | Negative Control | | Positive Control | | Patient's Sample | |
|---|---|---|---|---|---|---|
| Unrelated peptide | 0.23 | 0.15 | 0.29 | 0.35 | 1.36 | 1.15 |
| B. burgdorferi lysate | 0.25 | 0.21 | 2.45 | 2.68 | 1.41 | 1.54 |
| Outer surface protein-A + outer surface protein-C | 0.15 | 0.18 | 0.85 | 0.72 | 1.39 | 1.47 |
| Outer surface protein-E | 0.26 | 0.29 | 0.27 | 0.25 | 1.45 | 1.51 |
| Leukocyte function associated antigen | 0.18 | 0.15 | 1.84 | 1.65 | 1.53 | 1.49 |
| Immunodominant protein of invariable region | 0.19 | 0.17 | 2.34 | 2.10 | 1.25 | 1.36 |
| Variable major protein | 0.13 | 0.11 | 0.51 | 0.63 | 0.34 | 0.25 |
| Decorin binding protein of B.b. sensu stricto | 0.22 | 0.16 | 2.68 | 2.79 | 1.29 | 1.35 |
| Decorin binding protein of B. garinii | 0.23 | 0.18 | 0.19 | 0.22 | 1.65 | 1.79 |
| Decorin binding protein of B. afzelii | 0.15 | 0.24 | 0.43 | 0.39 | 1.25 | 1.18 |
| Babesia peptide | 0.18 | 0.16 | 0.17 | 0.22 | 1.41 | 1.35 |
| Ehrlichia peptide | 0.15 | 0.23 | 0.56 | 0.49 | 1.21 | 1.38 |

FIG.22

| Wells are coated with: | Negative Control | | Positive Control | | Patient's Sample | |
|---|---|---|---|---|---|---|
| Unrelated peptide | 0.28 | 0.35 | 0.31 | 0.35 | 0.99 | 1.15 |
| B. burgdorferi lysate | 0.26 | 0.22 | 1.84 | 1.98 | 1.25 | 1.05 |
| Outer surface protein-A + outer surface protein-C | 0.21 | 0.20 | 0.39 | 0.44 | 0.92 | 0.98 |
| Outer surface protein-E | 0.17 | 0.18 | 0.28 | 0.17 | 0.71 | 0.62 |
| Leukocyte function associated antigen | 0.21 | 0.25 | 0.31 | 0.25 | 0.65 | 0.74 |
| Immunodominant protein of invariable region | 0.27 | 0.29 | 1.95 | 1.76 | 0.76 | 0.87 |
| Variable major protein | 0.15 | 0.17 | 0.71 | 0.62 | 0.49 | 0.54 |
| Decorin binding protein of B.b. sensu stricto | 0.26 | 0.32 | 1.64 | 1.81 | 1.54 | 1.32 |
| Decorin binding protein of B. garinii | 0.17 | 0.19 | 0.49 | 0.56 | 1.47 | 1.42 |
| Decorin binding protein of B. afzelii | 0.25 | 0.22 | 0.35 | 0.32 | 0.92 | 1.05 |
| Babesia peptide | 0.27 | 0.21 | 0.49 | 0.62 | 1.96 | 1.78 |
| Ehrlichia peptide | 0.18 | 0.25 | 0.58 | 0.73 | 0.65 | 0.77 |

FIG. 23

```
                             SEQUENCE LISTING

<160> NUMBER OF SEQ ID NOS: 17

<210> SEQ ID NO 1
<211> LENGTH: 20
<212> TYPE: PRT
<213> ORGANISM: Borrelia LYME LFA

<400> SEQUENCE: 1

Glu Leu Gln Lys Lys Ile Tyr Val Ile Glu Gly Thr Ser Lys Gln Asp
 1               5                  10                  15

Leu Thr Ser Phe
            20

<210> SEQ ID NO 2
<211> LENGTH: 15
<212> TYPE: PRT
<213> ORGANISM: Borrelia LYME OspA

<400> SEQUENCE: 2

Ser Tyr Val Leu Glu Gly Thr Leu Thr Ala Glu Lys Thr Thr Leu
 1               5                  10                  15

<210> SEQ ID NO 3
<211> LENGTH: 25
<212> TYPE: PRT
<213> ORGANISM: Borrelia OspE-pep1

<400> SEQUENCE: 3

Ile Asn Asn Ser Ala Gly Gly Asp Lys Ile Ala Glu Tyr Ala Ile Ser
 1               5                  10                  15

Leu Glu Glu Leu Lys Arg Asn Leu Lys
            20                  25

<210> SEQ ID NO 4
<211> LENGTH: 25
<212> TYPE: PRT
<213> ORGANISM: Borrelia OspE-pep2

<400> SEQUENCE: 4

Ile Lys Thr Lys Ile Glu Lys Ile Asn Asp Thr Glu Tyr Ile Thr Phe
 1               5                  10                  15

Leu Gly Asp Lys Ile Asn Asn Ser Ala
            20                  25

<210> SEQ ID NO 5
<211> LENGTH: 19
<212> TYPE: PRT
<213> ORGANISM: Borrelia Lyme immunodominant C2 peptide

<400> SEQUENCE: 5

Asp Ala Ala Ser Val Asn Gly Ile Ala Lys Gly Ile Lys Gly Ile Val
 1               5                  10                  15
```

Asp Ala Ala

<210> SEQ ID NO 6
<211> LENGTH: 24
<212> TYPE: PRT
<213> ORGANISM: Lyme immunodominant C6 peptide

<400> SEQUENCE: 6

Lys Lys Asp Asp Gln Ile Ala Ala Ala Met Val Leu Arg Gly Met Ala
1               5                   10                  15

Lys Asp Gly Gln Phe Ala Leu Lys
            20

<210> SEQ ID NO 7
<211> LENGTH: 15
<212> TYPE: PRT
<213> ORGANISM: Borrelia Variable Major Protein Like Sequence-1

<400> SEQUENCE: 7

Ala Asn Asp Asn Ala Ala Lys Ala Ala Asp Lys Asp Ser Val Lys
1               5                   10                  15

<210> SEQ ID NO 8
<211> LENGTH: 17
<212> TYPE: PRT
<213> ORGANISM: Borrelia Variable Major Protein Like Sequence-2

<400> SEQUENCE: 8

Gly Gly Ser Glu Lys Leu Lys Ala Val Ala Ala Ala Lys Glu Asn Asn
1               5                   10                  15

Lys

<210> SEQ ID NO 9
<211> LENGTH: 30
<212> TYPE: PRT
<213> ORGANISM: Decorin binding protein-peptide from B. b. sensu o

<400> SEQUENCE: 9

Cys Gly Leu Thr Gly Ala Thr Lys Ile Arg Leu Glu Arg Ser Ala Lys
1               5                   10                  15

Asp Ile Thr Asp Glu Ile Asp Ala Ile Lys Lys Asp Ala Ala
            20                  25                  30

<210> SEQ ID NO 10
<211> LENGTH: 30
<212> TYPE: PRT
<213> ORGANISM: Decorin binding protein-peptide from B. garinii

<400> SEQUENCE: 10

Glu Lys Thr Pro Pro Thr Thr Ala Glu Gly Ile Leu Ala Ile Ala Gln
1               5                   10                  15

Ala Met Glu Glu Lys Leu Asn Asn Val Asn Lys Lys Gln Gln
            20                  25                  30

<210> SEQ ID NO 11
<211> LENGTH: 30
<212> TYPE: PRT
<213> ORGANISM: Decorin binding protein-peptide from B. afzelii

<400> SEQUENCE: 11

Ser Gly Ile Tyr Asp Leu Ile Leu Asn Ala Ala Lys Ala Val Glu Lys
1               5                   10                  15

```
Ile Gly Met Gln Gly Met Lys Gln Ala Val Glu Glu Ala Ala
            20                  25                  30

<210> SEQ ID NO 12
<211> LENGTH: 25
<212> TYPE: PRT
<213> ORGANISM: Babesia microti peptide

<400> SEQUENCE: 12

Ile Val Glu Phe Asn Ala Ile Phe Ser Asn Ile Asp Leu Asn Asn Ser
1               5                   10                  15

Ser Thr Val Lys Asn Glu Ile Ile Lys
            20                  25

<210> SEQ ID NO 13
<211> LENGTH: 23
<212> TYPE: PRT
<213> ORGANISM: Babesia bovis peptide

<400> SEQUENCE: 13

Val Glu Ala Pro Trp Tyr Lys Arg Trp Ile Lys Lys Phe Arg Asp Phe
1               5                   10                  15

Phe Ser Lys Asn Val Thr Gln
            20

<210> SEQ ID NO 14
<211> LENGTH: 19
<212> TYPE: PRT
<213> ORGANISM: Babesia equi peptide

<400> SEQUENCE: 14

Asp Phe Phe His Pro Glu Asp Val Val Ala Pro His Ser Gly Ile Thr
1               5                   10                  15

Thr Pro Lys

<210> SEQ ID NO 15
<211> LENGTH: 31
<212> TYPE: PRT
<213> ORGANISM: Ehrlichial N-terminal

<400> SEQUENCE: 15

Met Ser Ala Val Ser Asn Arg Lys Leu Pro Leu Gly Gly Val Leu Met
1               5                   10                  15

Ala Leu Val Ala Ala Val Ala Pro Ile His Ser Ala Leu Leu Ala
            20                  25                  30

<210> SEQ ID NO 16
<211> LENGTH: 30
<212> TYPE: PRT
<213> ORGANISM: Ehrlichial C-terminal

<400> SEQUENCE: 16

Val Ala Gly Ala Phe Ala Arg Ala Val Glu Gly Ala Glu Val Ile Glu
1               5                   10                  15

Val Arg Ala Ile Gly Ser Thr Ser Val Met Leu Asn Ala Cys
            20                  25                  30

<210> SEQ ID NO 17
<211> LENGTH: 15
<212> TYPE: PRT
<213> ORGANISM: Treponema palidum peptide
```

```
-continued

<400> SEQUENCE: 17

Arg Ser Glu Ala Met Ala Leu Val Leu Ser Thr Leu Glu Asn Arg
1               5                   10                  15
```

METHODS AND KIT FOR DIAGNOSING TICK BORNE ILLNESSES

BACKGROUND OF THE INVENTION

1. Field of the Invention

This invention relates to methods and kit for aid in diagnosing tick borne illnesses, including lyme. disease.

2. Description of the Related Art

Lyme disease is the most prevalent vector-borne disease of humans in the United States and is transmitted by the bite of Ixodes ticks. Infection is caused by the bacterium *Borrelia burgdorferi* resulting in an illness affecting various organ systems of the body. The clinical implications of Lyme disease can be seen in dermatologic, neurologic and rheumatologic manifestations. (1-5)

In Lyme disease two stages of the disease, acute and chronic, are considered. These stages may occur separately or may overlap. Neurological disorders (such as Bell's palsy, meningitis, encephalitis), cardiovascular cardiac arrhythmia, and disorders of the musculoskeletal system (migrating pain in muscles, tendons or joints) are possible in Lyme disease. If left untreated, the patient may acquire chronic lyme borreliosis. (6-8)

No matter what causes the manifestation of Lyme disease, the key to avoiding serious effects is prompt diagnosis and treatment of the underlying disorder. Early detection of Lyme disease is difficult because the characteristic rash is not evident. The flu-like symptoms which can be caused by many other factors are added to the severity of the problem. Many assays used in laboratories are unreliable. Therefore, it is advantageous to combine clinical symptomatology with a sensitive technique available to diagnose lyme disease. (9-15)

Lyme ELISA

The Lyme ELISA test is intended for the qualitative detection of IgG and IgM antibodies to *Borrelia burgdorferi* in human serum. Titers of IgG are generally low during the first weeks of illness. They peak three months to a year after infection and may remain elevated for years. Titers of IgM peak within three to six weeks after onset but are often not detectable in asymptomatic patients. (9,13,16)

Lyme Western Blot Assay.

The Western Blot Assay has been widely used to detect the presence of antibodies in human serum and plasma to various infectious disease agents. In this procedure, component proteins of purified, inactivated virus are electrophoretically separated by SDS-polyacrylamide electrophoresis followed by electrotransfer to nitrocellulose sheets. Each strip serves as the solid-phase antigen for an ELISA test.

Other Methods.

Culturing *Borrelia burgdorferi* from clinical samples other than *erythema migrans* lesions is difficult. PCR-based methods seem to be insensitive for routine lab testing due to absence or low number of bacteria in clinical samples.

The mainstay of laboratory diagnosis for Lyme disease has been Serological Assays. However due to antigenic diversity used in the assays their performance in different laboratories is highly variable (16-22).

The Western Blot Assay is more reliable since the cross-reactive antibodies are relatively excluded and peptide specific antibodies in the form of bands are observed. However, due to antigenic variations, if antibodies are not present in the blood, false negative results will be obtained (23-25).

SUMMARY OF THE INVENTION

In the embodiments, ELISA was combined with Western Blot, including the use of peptides from different components of *Borrelia* during different cycles and other tick-borne illness infective agents to increase the sensitivity and specificity of diagnosis of tick borne illnesses, including Lyme disease.

The embodiments provide a method for diagnosing exposure to a tick-borne disease in a patient, comprising the steps of:

determining a level of antibodies against peptides of infective agents from each of *Borrelia, Babesia*, and *Ehrlichia*, or corresponding recombinant antigens, or synthetic peptides thereof in a sample from said patient;

comparing the level of antibodies determined in step a) with normal levels of said antibodies from at least one healthy control, wherein normal levels of antibodies against *Borrelia, Babesia*, and *Ehrlichia* indicate optimal results;

higher than normal levels of antibodies against at least one peptide of *Borrelia* indicate a presence or possibility of an infection with an agent of Lyme disease, thereby diagnosing Lyme disease in the patient;

higher than normal levels of antibodies against peptides of *Babesia* indicate a presence or possibility of an infection with *Babesia*, thereby diagnosing babesiosis in the patient;

higher than normal levels of antibodies against peptides of *Ehrlichia*, indicate a presence or possibility of an infection with *Ehrlichia*, thereby diagnosing ehrlichiosis in the patient.

Another embodiment provides a kit for diagnosing exposure to a tick-borne disease in a patient comprising at least one peptide of infective agents from each of *Babesia*, and *Ehrlichia*, or corresponding recombinant antigens, or synthetic peptides.

Another embodiment provides for a kit for diagnosing exposure to a tick-borne disease in a patient comprising at least one peptide of infective agents from each of *Babesia*, and *Ehrlichia*, or corresponding recombinant antigens, or synthetic peptides, further comprising Borrelia, or corresponding recombinant antigens, or synthetic peptides.

BRIEF DESCRIPTION OF THE DRAWINGS

FIG. 1 shows a schematic of a microtiter plate with different rows (containing 12 wells each) which were coated with different peptides or antigens.

FIG. 6 shows a chart of IgG antibody levels against 12 different peptides and antigens in negative control, positive control specimens and Case #1.

FIG. 7 shows a chart of IgM antibody levels against 12 different peptides and antigens in negative control, positive control specimens and Case #1.

FIG. 10 shows a chart of IgG antibody levels against 12 different peptides and antigens in negative control, positive control specimens and Case #2.

FIG. 11 shows a chart of IgM antibody levels against 12 different peptides and antigens in negative control, positive control specimens and Case #2.

FIG. 14 shows a chart of IgG antibody levels against 12 different peptides and antigens in negative control, positive control specimens and Case #3.

FIG. 15 shows a chart of IgM antibody levels against 12 different peptides and antigens in negative control, positive control specimens and Case #3.

FIG. 18 shows a chart of IgG antibody levels against 12 different peptides and antigens in negative control, positive control specimens and Case #4.

FIG. 19 shows a chart of IgM antibody levels against 12 different peptides and antigens in negative control, positive control specimens and Case #4.

FIG. 22 shows a chart of IgG antibody levels against 12 different peptides and antigens in negative control, positive control specimens and Case #5.

FIG. 23 shows a chart of IgM antibody levels against 12 different peptides and antigens in negative control, positive control specimens and Case #5

DETAILED DESCRIPTION OF THE PREFERRED EMBODIMENT

Figure 2:
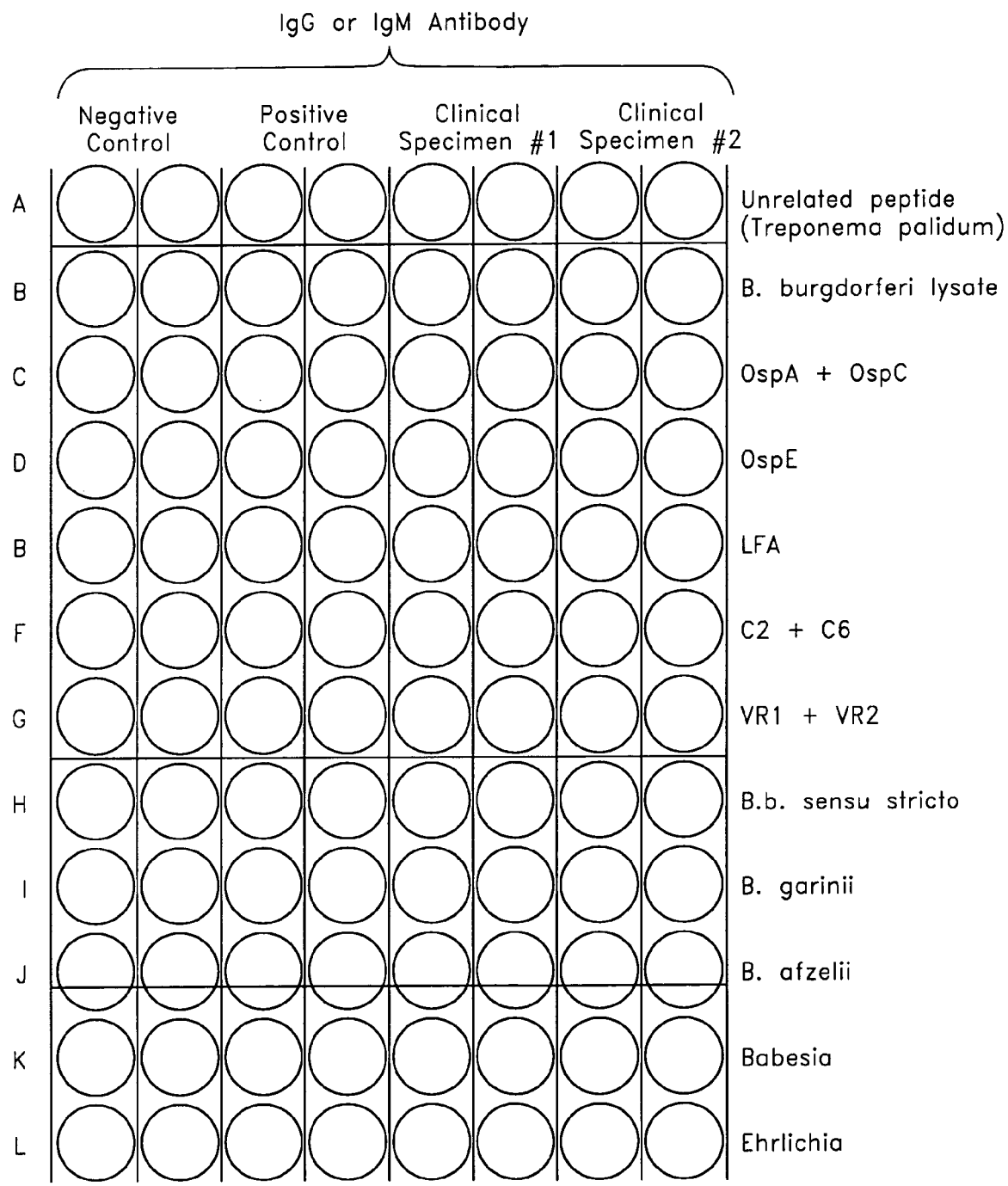
FIG. 2 shows a schematic of a microtiter plate of a Multi-Peptide ELISA-blot IgG and IgM assay against different peptides and proteins of *Borrfelia burgdorferi*.

Prompt diagnosis and treatment of Lyme disease is the key to avoiding chronic lyme borreliosis and its serious effect on the human system. Therefore, it is advantageous to combine clinical symptomatology with a sensitive technique available to diagnose Lyme disease. In search of a sensitive method, ELISA, Western Blot, and the newly developed peptide-based ELISA were applied to clinical specimens from patients with clinical symptoms of Lyme disease. Since the chronic nature of Lyme disease and antigenic diversity of the spirochetes suggest that antigenic variation plays an important role in immune invasion, peptides from different components of *Borrelia* during different cycles, including peptides from outer surface protein, leukocyte function associated antigens, immunodominant antigens, variable major proteins, and peptides from decorin-binding proteins of Borrelial subspecies (*B. sensu stricto. B. afzelii, B. garinii*) were utilized. Furthermore, in the same ELISA assay, antibodies against specific peptides from *Babesia* and *Ehrlichia* in order to exclude cross-reactive antibodies were measured. The measured antibodies can also be bound to their specific antigens and form immune complexes against said peptides and antigens.

There are other organisms besides *Borrelia* that live in ticks and can be transmitted to humans through bites, causing other tick-borne illnesses (TBI). The most common ones known to date include *Babesia* (babesiosis) and *Erhlichia* (erhlichiosis). *Babesia* and *Erhlichia* are also spirochetes, as is *Borrelia*. The symptoms of other TBI often overlap those of Lyme disease and, like Lyme disease, are just as difficult to diagnose and treat. Preferred embodiments can distinguish Lyme disease as a result of infection with *Borrelia* from other tick-borne illnesses. Alternatively, preferred embodiments can distinguish tick-borne illnesses, such as *babesiosis* and *erlichiosis*, from Lyme disease as a. result of infection with Borrelia.

While correlation between specimens positive by Western Blot and multi-peptide ELISA is more than 95%, the Multi-Peptide ELISA has the following advantages over the Western Blot:

Multi-Peptide ELISA is more sensitive than Western Blot, since with Multi-Peptide ELISA samples with equivocal or negative results can be confirmed or reclassified.

Multi-Peptide ELISA is quantitative, and is expressed either by optical densities or by index values (division of O.D. of clinical specimen by O.D. of negative control).

Multi-Peptide ELISA is species and subspecies specific, because antibodies are measured against peptides of *B. sensu stricto, B. garinii and B. afzelii*.

Multi-Peptide ELISA detects antibodies against *Babesia* and *Ehrlichia*. Very often *Babesia* and *Ehrlichia* are transmitted along with *Borrelia* by the same tick, and this method can detect antibodies against all three spirochetes simultaneously.

Multi-Peptide ELISA can detect antibodies against unrelated peptides (*Treponema palidum*). This measurement excludes possible cross-reactive antibodies.

The preferred embodiments disclose methods and kits for detecting the presence of antibodies in human or animal bodily fluids, including, but not limited to, blood, serum, plasma, urine, colostrum, milk, tears, or saliva.

Combination of ELISA with Western Blot using Antigens or Peptides from various regions of *Borrelia*.

The chronic nature of Lyme disease and antigenic diversity of the spirochetes suggests that antigenic variation plays an important role in immune evasion. Surface major proteins or lipoproteins called VMP or VIsE are responsible for this antigenic variation strategy evolved by pathogenic microbes to avoid immune destruction (26-30). Since peptides are highly pure, there is no need for separation by SDS-gel electrophoresis. Furthermore, different membrane surface protein E (OSPE) enables the microorganism to evade the immune system and to maintain chronic infection (31-35). Accordingly, peptides from different components of *Borrelia* during different life cycles can be used.

Selection of Peptides from Outer Surface Protein and Leukocyte Function Associated Antigen A prominent late manifestation of *Borrelia burgdorferi* is Lyme arthritis. Antibody reactivity to outer surface protein A (OspA) and outer surface protein C (OspC) typically develops near the beginning of prolonged episodes of arthritis. These patients may progress to autoimmune state by developing a cross-reactive response between OspA and OspC and a self antigen. Therefore treatment-resistant Lyme arthritis is associated with immune reactivity to OspA and OspC of *Borrelia* and the major Histocompatibility Complex II Allele DRB1. A gene bank search revealed a peptide from human leukocyte function-associated antigen-1 (hLFA-1) as a candidate autoantigen. Individuals with treatment-resistant Lyme arthritis, but not other forms of arthritis, generated responses to OspA and OspC, hLFA-1, and their highly related peptide epitopes. Identification of the initiating bacterial antigen and a cross-reactive autoantigen may provide a model for development of autoimmune disease. (36)

Amino acid sequence of peptides selected from Leukocyte function associated antigen and outer surface protein-A are shown below:

```
LYME LFA = ELQKKIYVIEGTSKQDLTSF    (SEQ ID NO:1)
LYME OspA = SYVLEGTLTAEKTTL        (SEQ ID NO:2)
```

Peptides from outer surface protein E involved in immune evasion

The ability of the Lyme spirochete to maintain chronic infection indicates that the organism is capable of immune evasion. The immune evasion of Lyme disease spirochetes is done by either antigenic variation or through the binding of Complement Regulatory Protein Factor H. The OspE is surface-exposed and is expressed in both ticks and mammals, and elicit a strong antibody response. Analysis of the specificity of the antibody response to different OspE variants suggests that it is the hypervariable regions that are targeted by antibody response during infection. On the other hand it is the conserved regions of OspE that are involved in Complement Regulatory Protein Factor H. Some of these proteins (FH-like Protein1/Reconectin) serve as cofactors for Factor 1 mediated degradation of C3b Complement. Degradation of C3b results in decreased levels of the C3 Convertase Complex, which facilitates complement evasion. Therefore it is important to assess the specificity of the antibody response to OspE epitopes that are exposed during infection (35- 38). Two different OspE peptides that span C terminal of BBL39 were used for antibody studies:

```
OspE-pep1, INNSAGGDKIAEYAISLEELKRNLK    (SEQ ID NO:3)
OspE-pep2, IKTKIEKINDTEYITFLGDKINNSA    (SEQ ID NO:4)
```

Peptides from Immunodominant Antigens

The spirochete that causes Lyme disease expresses a surface lipoprotein called Variable Major Protein (VMP) or Variable Major Protein Like Sequence (VLSE). A 19-mer peptide (C2 peptide) and 25-mer (C6 peptide) are clearly conserved across both genospecies and strains of *B. burgdorferi, Sensu lato: Sensu stricto* and *B. gariniii* (30). Amino acid sequences of these peptides are shown below:

```
Lyme immunodominant C2 peptide:
DAASVNGIAKGIKGIVDAA                    (SEQ ID NO:5)
```

```
Lyme immunodominant C6 peptide:
KKDDQIAAAMVLRGMAKDGQFALK               (SEQ ID NO:6)
```

Antigenicity of this peptide was confirmed in humans, monkeys, and mice. Sera from all these hosts reacted with C2 and C6 peptide early and persistently in the course of infection, thus indicating that these peptides contain one or more epitopes that are broadly antigenic.

The antigenicity of these peptides not only manifest independently of host species, but also regardless of animal infection with different strains of *B. b sensu stricto*. Thirty-five of 41 human serum samples collected in the northeast and midwest of the U.S. from patients with acute or chronic Lyme disease reacted with C6 peptide and presented significant levels of antibodies against this 25-mer peptide. The five serum samples that had no detectable anti-C6 antibody were obtained from patients who were in the early stage of infection. This peptide-based ELISA was found to have diagnostic sensitivities of 74% in acute or early stage of Lyme disease (29,30)

Peptides from Variable Major Protein and Immune Response to Variable Major Protein-Like Sequence (VIsE) During Infection with Lyme Disease Spirochetes.

Infection-induced sequence changes that alter the antigenic properties of VlsE contributes to immune evasion. In experimental model a strong anti-VlsE IgG response was shown by fourth week of infection, indicating that VIsE is expressed during early stage of infection. All variants of *B. burgdorferi* were recognized by antibodies that developed against VIsE (29). These antibodies were reactive against relapsing fever spirochetes *B. hermsii, B. parkeri,* and *B. turicatae*. Serum samples from human Lyme disease patients also possessed anti-VIsE antibodies that were immunoreactive against all species of *Borellia*. These observations indicate that there are conserved Epitopes among VIsE variants that are antigenic during infection in humans. Most Lyme disease patients develop anti-VIsE antibody response. Based on this, researchers employed recombinant VIsE in ELISA format and demonstrated diagnostic sensitivities of 63% for culture-confirmed *erythema migrans* cases and 92% for late stage infections (35-37). The following two peptides selected from antigens expressed during the early stage of infection were used in this assay:

```
Variable Major Protein Like Sequence-
1:
ANDNAAKAADKDSVK                        (SEQ ID NO:7)
```

```
Variable Major Protein Like Sequence-
2:
GGSEKLKAVAAAKENNK                      (SEQ ID NO:8)
```

Peptides from Decorin Binding Protein for Species-Specific Serodiagnosis of Lyme Arthritis and Neuroborreliosis.

In the United States Lyme borreliosis is caused by a subspecies, *B. burgdorferi* sensu stricto. In Europe, however, three different Borrelial subspecies, *B. burgdorferi* sensu stricto, *B afzelii,* and *B. garinni,* are known etiologic agents of Lyme disease. Among individual *Borrelial* proteins from different species, sequence heterogeneity varies up to 40% (39-

44). Decorin binding protein A, a *Borrelial* outer surface protein, is one of the key proteins in *B. burgdorferi*. This antigen elicits a strong antibody response during experimental murine *Borreliosis* and has been suggested as a potential vaccine protein (46,47). This protein was cloned and sequenced from the three pathogenic *Borrelia* species common in the U.S. and in Europe (48,49).

```
Decorin binding protein-peptide from
B. b.sensu stricto:
CGLTGATKIRLERSAKDITDEIDAIKKDAA        (SEQ ID NO:9)

Decorin binding protein-peptide from
B. gariniii:
EKTPPTTAEGILAIAQAMEEKLNNVNKKQQ        (SEQ ID NO:10)

Decorin binding protein-peptide from
B. afzelii:
SGIYDLILNAAKAVEKIGMQGMKQAVEEAA        (SEQ ID NO:11)
```

The respective recombinant proteins were produced and tested as antigens by ELISA. In a recent study (48) one hundred percent of patients with neuroborreliosis (NB) and 93% of patients with Lyme arthritis (LA) reacted positively with these peptides. Sera from the majority of patients reacted with one rDbpA only and had no or low cross-reactivity to other two variant proteins. In patients with culture-positive *erythema migrans* (EM), the sensitivity of rDbpA immunoglobulin G (IgG) or IgM ELISA was low. The DbpA seems to be a sensitive and specific antigen for the serodiagnosis of Lyme arthritis or neuroborreliosis, but not of *Erythema migrans* (48).

Simultaneous Measurement of Antibody against *Borrelia* and *Babesia*.

*Babesia* species represent some of the most common infectious parasites among wild and domestic animals and are gaining increasing interest as emerging causes of zoonoses in humans. They require competent nonvertebrate and vertebrate hosts to maintain transmission cycles, infecting ixodid ticks and vertebrate erythrocytes. Several species have been shown to infect humans, although *Babesia microti* is the species most frequently identified. Although the parasite was originally identified as being endemic to the northeastern United States and parts of the Midwest, new reports have expanded the distribution to as far south as New Jersey in the United States and many parts of Europe and Japan. In the United States, *B. microti* is naturally transmitted by the deer tick *Ixodes scapularis* (also called *Ixodes dammini*), which acquires its infection from the white-footed mouse, *Peromyscus leucopus*. *Babesia caballi*, like *Babesia equi*, is a tick-borne protozoan parasite which causes fever, anemia, jaundice, and edema in the infected horses and sometimes results in death. Clinical signs in animals and in humans are not specific diagnostic measures for babesiosis, especially in asymptomatic or mixed infection in areas of endemicity. Therefore, serological distinction of these infections is very important for choice of prophylactic treatment (50-53).

One embodiment is the development of a highly specific and sensitive diagnostic system for *Babesi*. ELISA using the whole lysates of *B. caballi*—infected erythrocytes was found to cause an extensive cross-reaction between *B. caballi* and *B. equi* infected horse sera. Competitive-inhibition ELISA using recombinant antigens was also developed for the detection of *B. equi* and *B caballi* infections (54,55). An ELISA system that could specifically detect anti-*Babesia* antibodies by using an immunodominant peptide originated from merozoite antigens was developed. The peptide-based ELISA is a potential diagnostic antibody in the detection of *Babesia* y infection. The following species-specific *Babesia* peptides are used in our assay:

```
Babesia microti
IVEFNAIFSNIDLNNSSTVKNEIIK             (SEQ ID NO:12)

Babesia bovis
VEAPWYKRWIKKFRDFFSKNVTQ               (SEQ ID NO:13)

Babesia equi
DFFHPEDVVAPHSGITTPK                   (SEQ ID NO:14)
```

Simultaneous Measurement of Antibodies against *Borrelia* and *Ehrlichial* Pathogens Members of the order Rickettsiales constitute a diverse group of obligatory intracellular bacteria of eukaryotic cells, including *Rickettsia, Orientia, Anaplasma, Ehrlichia, Neorickettsia, Bartonella* and *Coxiella*. The *Ehrlichiae*, which were recognized until recently primarily as agents of a disease of canines and equines in the United States, have now been shown to be agents of human monocytic ehrlichiosis (HME) and, more recently, human granulocytic ehrlichiosis (HGE). Genogroup II *ehrlichia*, including the agent of human granulocytic ehrlichiosis, *Ehrlichia phagocytophila*, and the bovine pathogen *Anaplasma marginale*, express a markedly immunodominant outer membrane protein designated major surface protein 2 (MSP2). MSP2 is encoded by a multigene family, resulting in the expression of variant B cell epitopes. MSP2 variants are sequentially expressed in the repeated cycles of rickettsemia that characterize persistent A. marginale infection and control of each rickettsemic cycle is associated with development of a variant-specific IgG response. Control of rickettsemia during persistence could result from an anamnestic Th lymphocyte response to conserved regions of MSP2 that enhances the primary Ab response against newly emergent variants (56, 57). Therefore, measurements of IgG and IgM antibody against these highly conserved regions of MSP2 is the best method for assessing humoral immune response against ehrlichial pathogens.

Overlapping peptides that span the N and C termini of *Anaplasma marginale* and *Anaplasma ovis* were used in this study:

```
Ehrlichial N-terminal:
MSAVSNRKLPLGGVLMALVAAVAPIHSALLA       (SEQ ID NO:15)

Ehrlichial C-terminal:
VAGAFARAVEGAEVIEVRAIGSTSVMLNAC        (SEQ ID NO:16)
```

Measurement of Antibodies against Unrelated Spirochete Peptides

*Treponema palidum* was used as a spirochete unrelated to *Borrelia* for possible detection of cross-reactive antibodies.

The following *Treponema* peptide was used in our assay:

```
Treponema palidum:
RSEAMALVLSTLENR                       (SEQ ID NO:17)
```

EXAMPLE 1

Comparison of EIA, Western Blot and Multi-Peptide ELISA-Blot Materials and Methods Amino acid sequences of peptides selected from *Borrelia, Babesia, Ehrlichia* and *Treponema* peptides used in this study are shown below:

```
Outer Surface Protein-A Peptide
Lyme OspA
SYVLEGTLTAEKTTL                       (SEQ ID NO:2)

Outer Surface Protein-E Peptide
Lyme OspE-pep1,
INNSAGGDKIAEYAISLEELKRNLK             (SEQ ID NO:3)

Lyme OspE-pep2,
IKTKIEKINDTEYITFLGDKINNSA             (SEQ ID NO:4)

Leukocyte Function Associated
Antigen
LYME LFA = ELQKKIYVIEGTSKQDLTSF       (SEQ ID NO:1)

Immunodominant Protein of Invariable
Region
Lyme C2 peptide:
DAASVNGIAKGIKGIVDAA                   (SEQ ID NO:5)

Lyme C6 peptide:
KKDDQIAAAMVLRGMAKDGQFALK              (SEQ ID NO:6)

Variable Major Protein
Variable Major Protein Like
Sequence-1:
ANDNAAKAADKDSVK                       (SEQ ID NO:7)

Variable Major Protein Like
Sequence-2:
GGSEKLKAVAAAKENNK                     (SEQ ID NO:8)

Borrelia Species Specific Decorin
Binding Protein
Decorin binding protein-peptide from
B. b.sensu stricto:
CGLTGATKIRLERSAKDITDEIDAIKKDAA        (SEQ ID NO:9)

Decorin binding protein-peptide from
B. garinii:
EKTPPTTAEGILAIAQAMEEKLNNVNKKQQ        (SEQ ID NO:10)

Decorin binding protein-peptide from
B. afzelii:
SGIYDLILNAAKAVEKIGMQGMKQAVEEAA        (SEQ ID NO:11)

Babesia Peptides
Babesia microti
IVEFNAIFSNIDLNNSSTVKNEIIK             (SEQ ID NO:12)

Babesia bovis
VEAPWYKRWIKKFRDFFSKNVTQ               (SEQ ID NO:13)

Babesia equi
DFFHPEDVVAPHSGITTPK                   (SEQ ID NO:14)

Ehrlichia Peptides
Ehrlichial N-terminal
MSAVSNRKLPLGGVLMALVAAVAPIHSALLA       (SEQ ID NO:15)

Ehrlichial C-terminal
VAGAFARAVEGAEVIEVRAIGSTSVMLNAC        (SEQ ID NO:16)

Treponema Palidum
RSEAMALVLSTLENR                       (SEQ ID NO:17)
```

These peptides at high-performance liquid chromatography grade were synthesized by Bio-Synthesis, Inc. (Lewisville, Tex.). All other chemicals and reagents were purchased from Sima-Aldrich (St. Louis, Mo.).

Clinical Specimens:

Sera from 12 healthy controls and 12 patients with Lyme disease confirmed by more than 300 laboratories participating in surveys conducted by the College of American Pathologists and the New York Department of Health. In addition, 103 clinical specimens from patients with signs and symptoms of Lyme disease were obtained from different clinics.

Multi-Peptide ELISA Blot for detection of antibodies against different specific and non-specific peptides and antigens.

Different rows (containing 12 wells each) of a microtiter plate were coated with different peptides or antigens in the order shown in FIG. 1. Antigens and peptides were dissolved either in phosphate buffer saline (PBS) or methanol at a concentration of 1.0 mg/mL and then diluted 1:100 in 0.1 M carbonate buffer (pH 9.5), and 100 µl was added to each well of polystyrene flat-bottom ELISA plates. Plates were incubated overnight at 4° C. and then washed three times with 200 µl of Tris-buffered saline (TBS) containing 0.05% Tween 20, pH 7.4. The non-specific binding of immunoglobulins (Igs) was prevented by adding a mixture of 1.5% bovine serum albumin (BSA) and 1.5% gelatin in TBS; and then incubating this mixture for 2 h at room temperature and then overnight at 4° C. Plates were washed as described above, then dried and kept in plastic bags at room temperature until used. Serum samples were diluted 1:200 in 1% BSA+HSA containing Tween 20, and 1 mg/mL FC fragments (to avoid reactivity of specific antibodies with rheumatoid factor) were added to duplicate wells of each row and incubated for 1 hour at room temperature. Serum from a healthy individual with negative antibodies to *Borrelia* and serum from a patient confirmed with Lyme disease and with very high levels of IgG and IgM antibodies against *Borrelia* were used as negative and positive controls. Plates were washed, and then alkaline phosphatase-conjugated goat anti-human IgG or IgM F(ab')$_2$ fragments (KPI, Gaithersburg, Md.) at an optimal dilution of 1:400 to 1:2,000 in 1% HSA-TBS was added to each well; the plates were then incubated for an additional 2 h at room temperature. After washing five times with TBS-Tween buffer (1 mg/mL) containing 1 mM MgCl$_2$ and sodium azide, pH 9.8. the reaction was stopped 45 mins later with 50 µl of 1 N NaOH. The optical density was read at 405 nm (OD$_{405}$) with a microtiter reader.

Commercially available Enzyme Immunoassay (EIA) and Western Blot for detection of IgG and IgM against *Borrelia burgdorferi*.

IgG and IgM EIA and IgG and IgM Marblot were purchased from MarDx, Carlsbad, Calif., USA.

Multi-Peptide ELISA-Blot Assay.

The Multi-Peptide ELISA-blot IgG and IgM assay against different peptides and proteins of *Borrfelia burgdorferi* was performed as shown in FIG. 2.

Comparison of EIA, Western Blot and Multi-Peptide ELISA-Blot

For comparison, first we applied these assays to 24 specimens, which according to the College of American Pathologists and the New York Department of Health surveys, were classified as positive (12 specimens) or negative (12 specimens) for Lyme disease. Of 12 specimens with either positive IgG, IgM, or IgG and IgM, the titer of antibodies did not correlate at all with the number of bands in the Western Blot Assay and with our multi-peptide ELISA assay. For example, a sample with an ELISA IgG level of 133 (shown in Table 2, Sample #11) resulted in more bands in the Western Blot Assay than a sample with an ELISA IgG level of 995 (Table 2, Sample #2).

When these specimens were tested with multi-peptide ELISA, similar results were also obtained. Antibodies against four peptides were positive when serum with IgG ELISA level of 133 was used, while only two peptides were positive when serum with IgG level of 995 was applied. Moreover, out of 12 specimens with low IgG and IgM ELISA, 2 specimens were found to be positive for IgM Blot Assay with 23, 45 and 58 kDa bands. Interestingly, the same 2 specimens were positive for IgM against immunodominant protein of invariable region, variable major protein, and decorin-binding protein of *B. sensu stricto* (Tables 1 and 2). These findings led us to conclude that ELISA-based *Borrelia* lysate antigens and Western Blot may suffer from both false positive and false negative results, and that only a comparison of the present multi-peptide based ELISA assay to the Western Blot might result in a more sensitive, more specific assay for detection of Lyme disease.

As stated above, serum from a healthy individual with negative antibodies to *Borrelia* and serum from a patient confirmed with Lyme disease and with very high levels of IgG and IgM antibodies against *Borrelia* were used as negative and positive controls. A normal level of antibody is defined as a level of antibody taken from a healthy control individual or an average level of antibody taken from a set of healthy control individuals. A level can be more than two standard deviations of an average level of antibody taken from a set of healthy control individuals.

TABLE 1

Performance of Western Blot and Multi-Peptide ELISA assays on 12 different specimens that were classified negative for Lyme antibodies by 340 laboratories participating in a survey conducted by the College of American Pathologists.

|  | ELISA | | Western Blot | | Multi-Peptide ELISA | | | | | | | |
|---|---|---|---|---|---|---|---|---|---|---|---|---|
|  | | | | | *Borrelia* Peptides | | *Babesia* Peptide | | *Erlichia* Peptides | | Unrelated Peptides | |
| Sample # | IgG | IgM | IgG | IgM | IgG | IgM | IgG | IgM | IgG | IgM | IgG | IgM |
| 1 | 15 | 14 | + | − | − | − | − | − | − | − | − | − |
| 2 | 12 | 10 | − | − | − | − | − | − | − | − | − | − |
| 3 | 15 | 25 | − | 2+ | + | 2+ | − | − | − | − | − | − |
| 4 | 10 | 20 | + | − | − | + | − | − | − | − | − | − |
| 5 | 50 | 52 | + | 2+ | − | 4+ | − | − | − | − | − | − |
| 6 | 56 | 30 | + | − | + | + | + | + | − | − | − | − |
| 7 | 59 | 43 | + | 2+ | + | 3+ | + | − | − | − | − | − |
| 8 | 39 | 24 | + | + | − | + | − | − | − | − | − | − |
| 9 | 43 | 54 | + | − | − | + | − | − | − | − | − | − |
| 10 | 67 | 93 | + | + | − | + | − | − | − | − | − | − |
| 11 | 15 | 20 | − | − | + | − | − | − | − | − | − | − |
| 12 | 12 | 10 | − | − | − | − | − | − | − | − | − | − |

TABLE 2

Performance of Western Blot and Multi-Peptide ELISA assays on 12 different clinical specimens that were classified positive for Lyme antibodies by 340 laboratories participating in a survey conducted by the College of American Pathologists.

|  | ELISA | | Western Blot | | Multi-Peptide ELISA | | | | | | | |
|---|---|---|---|---|---|---|---|---|---|---|---|---|
|  | | | | | *Borrelia* Peptides | | *Babesia* Peptides | | *Ehrlichia* Peptides | | Unrelated Peptides | |
| Sample # | IgG | IgM | IgG | IgM | IgG | IgM | IgG | IgM | IgG | IgM | IgG | IgM |
| 1 | 770 | 130 | 2+ | 1+ | 3+ | 2+ | − | − | − | − | − | − |
| 2 | 995 | 105 | 2+ | 1+ | 2+ | 1+ | − | − | − | − | − | − |
| 3 | 223 | 230 | 1+ | − | 2+ | − | + | − | − | − | − | − |
| 4 | 190 | 194 | 3+ | 4+ | 2+ | 6+ | − | − | − | − | − | − |
| 5 | 289 | 121 | 2+ | 2+ | 1+ | 4+ | − | − | − | − | − | − |
| 6 | 246 | 298 | 3+ | 4+ | 2+ | 6+ | − | + | − | − | − | − |
| 7 | 280 | 156 | 1+ | 3+ | 1+ | 5+ | − | − | − | − | − | − |
| 8 | 164 | 30 | 2+ | 1+ | 1+ | 3+ | − | − | − | − | − | − |
| 9 | 10 | 136 | − | 1+ | − | 2+ | − | − | − | − | − | − |
| 10 | 233 | 478 | 3+ | 2+ | 4+ | 2+ | − | − | − | − | − | − |
| 11 | 133 | 316 | 4+ | 3+ | 5+ | 5+ | − | − | − | − | − | − |
| 12 | 85 | 344 | 2+ | 3+ | 2+ | 4+ | − | + | + | + | − | − |

This comparision was applied to 103 different specimens from patients presenting symptoms of Lyme disease mainly from two different clinics, one from the east coast and the other from the west coast.

Figure 3:
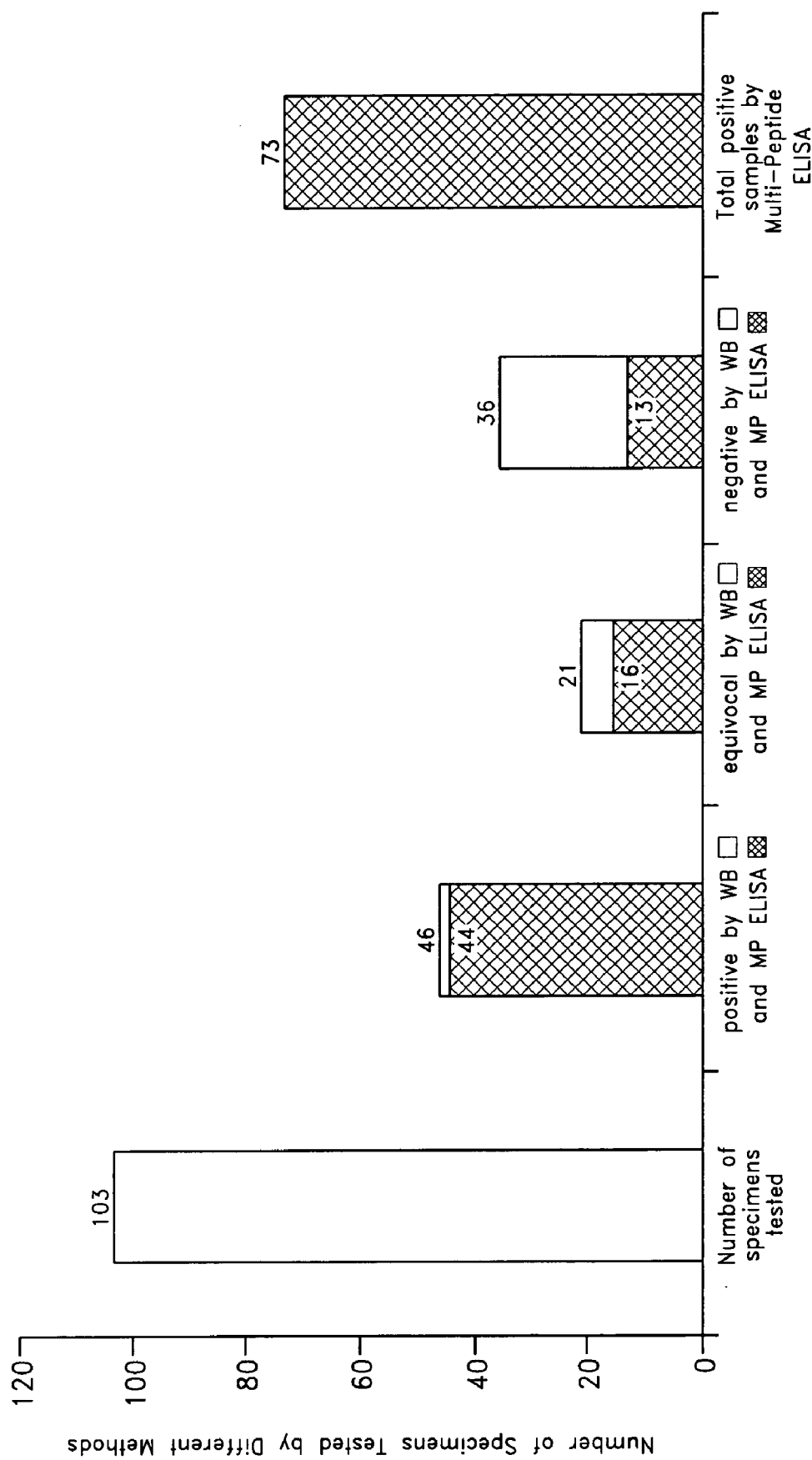
FIG. 3 shows a graph of classification of specimens from patients with symptoms of Lyme disease to positive, equivocal or negative by Western blot and Multi-Peptide (MP) ELISA.

Based on CDC criteria and detection of 5 out of 11 bands for IgG and 2 out of 3 bands for IgM, 46 out of 103 (45%) specimens were classified as positive, 21 or 20% of specimens that showed 3-4 bands for IgG and one band for IgM were classified as equivocal (or intermediate), and 36 (35%) specimens with either no bands or 1-2 faint bands were classified as negative. When multi-peptide ELISA was applied to these specimens, out of 46 positive specimens by Western Blot, 44 were highly positive (96% correlation) and two equivocal (FIG. 3). Furthermore, 16 out of 21 equivocal samples classified by Western Blot reacted highly with *Borrelia*-purified antigens and peptides selected from outer surface proteins, immunodominant proteins, and leukocyte function associated antigens, and one of three species of specific peptides (*B. sensu stricto, B. garinii* and *B. afzelii*).

Figure 4:
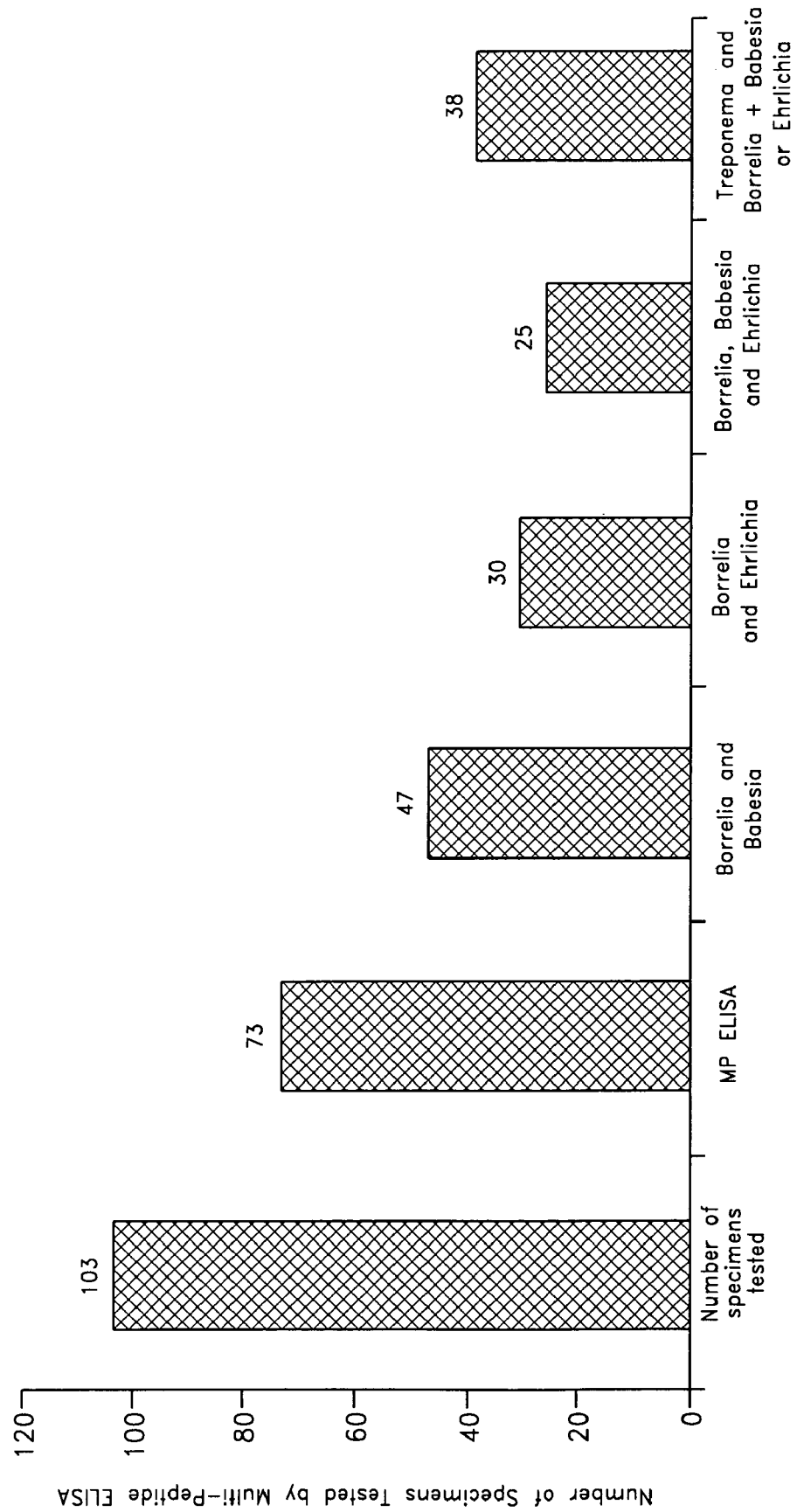
FIG. 4 shows a graph of number of specimens tested by Multi-Peptide (MP) ELISA that are positive for various antigens.

Moreover, 13 out of 36 Western Blot negative specimens were clearly reacted with 3-5 antigens and peptides (FIG. 3) to examine whether or not antibodies detected against *Borrelia* antigens and peptides are due to cross-reaction with other spirochetes. We applied these sera to an unrelated peptide (*Treponema palidum*), as well as to *Babesia* and *Ehrlichia* 1 peptides. Out of 73 specimens positive by multi-peptide ELISA, 47 were positive for *Babesia*, 30 for *Ehrlichia*, 25 for *Babesia* and *Ehrlichia*, and 38 for *Treponema*-peptide-specific antibodies (FIG. 4). It is interesting to note that all 38 specimens reacted with *Treponema* peptide antigens were reactive with either combinations of *Babesia* or *Ehrlichia* and *Borrelia* antigens or peptides (Tables 3, 4). These results show that simultaneous detection of antibodies against *Borrelia, Babesia, Ehrlichia* and *Treponema* can indicate cross-infection with multiple organisms, or that these antibodies are produced against *Borrelia*, but cross-react with different spirochetes. Clarification of these possible cross-reactive antibodies deserves investigation.

TABLE 3

Measurements of IgG and IgM antibodies by Western Blot and Multi-Peptide ELISA against *Borrelia burgdorferi* antigens and peptides in patients with symptoms of Lyme disease. Possible cross-reaction with *Babesia*, *Ehrlichia* and unrelated peptides from *Treponema palidum*

| | Western Blot | | Multi-Peptide ELISA | | | | | | | |
|---|---|---|---|---|---|---|---|---|---|---|
| | | | *Borrelia* Peptides | | *Babesia* Peptides | | *Ehrlichia* Peptides | | Unrelated Peptides | |
| Sample # | IgG | IgM | IgG | IgM | IgG | IgM | IgG | IgM | IgG | IgM |
| 1 | 2+ | 1+ | − | − | + | + | − | − | − | − |
| 2 | 4+ | 1+ | 4+ | 1+ | + | + | − | − | − | − |
| 3 | 4+ | 2+ | 6+ | 1+ | + | + | − | − | − | − |
| 4 | 1+ | 4+ | 6+ | 6+ | − | − | − | − | − | − |
| 5 | 8+ | 4+ | 5+ | 5+ | + | + | − | − | − | + |
| 6 | 8+ | 3+ | 3+ | 7+ | − | − | − | − | − | − |
| 7 | 6+ | 5+ | 6+ | 10+ | + | + | − | − | − | + |
| 8 | 1+ | 1+ | 5+ | 7+ | − | + | − | − | − | − |
| 9 | 1+ | 1+ | − | 1+ | − | − | − | − | − | − |
| 10 | 5+ | 2+ | 2+ | 1+ | − | − | − | − | − | − |
| 11 | 3+ | 3+ | 1+ | 5+ | − | − | − | − | − | − |
| 12 | 6+ | 2+ | 6+ | 3+ | + | + | − | − | − | − |
| 13 | 2+ | 4+ | 5+ | 5+ | − | − | − | + | − | − |
| 14 | − | − | − | − | − | − | − | − | − | − |
| 15 | 6+ | 2+ | 5+ | 1+ | + | + | + | + | + | − |
| 16 | 3+ | − | 4+ | 2+ | − | − | − | − | − | − |
| 17 | − | − | − | − | − | − | − | − | − | − |
| 18 | 1+ | 1+ | − | − | − | − | − | − | − | − |
| 19 | 4+ | 5+ | 3+ | − | − | − | − | − | − | − |
| 20 | 2+ | 1+ | 4+ | 3+ | + | + | + | + | + | + |
| 21 | 3+ | 5+ | 7+ | 9+ | + | + | + | + | + | + |
| 22 | 1+ | − | 2+ | 1+ | + | + | + | + | − | − |
| 23 | − | − | − | − | − | − | − | − | − | − |
| 24 | − | − | − | − | − | − | − | − | − | − |
| 25 | 4+ | 1+ | 3+ | − | − | − | − | − | − | − |
| 26 | − | − | − | − | − | − | − | − | − | − |
| 27 | − | − | − | − | − | − | − | − | − | − |
| 28 | 1+ | 3+ | 5+ | 3+ | − | − | + | + | + | + |
| 29 | − | 2+ | − | 1+ | − | − | + | + | − | − |
| 30 | 3+ | 2+ | 9+ | 2+ | + | − | + | − | + | − |
| 31 | − | 2+ | 1+ | 3+ | − | − | − | − | − | − |
| 32 | − | 2+ | − | 2+ | − | − | − | − | − | − |
| 33 | 2+ | 4+ | 2+ | 9+ | + | + | − | + | + | − |
| 34 | 5+ | 1+ | 4+ | 6+ | − | + | − | − | − | − |
| 35 | 6+ | 1+ | 3+ | 6+ | − | + | − | − | − | − |
| 36 | 5+ | 5+ | 6+ | 9+ | − | + | − | + | + | + |
| 37 | 7+ | 2+ | 4+ | 1+ | − | − | − | − | − | − |
| 38 | 3+ | 1+ | 2+ | 7+ | − | − | − | − | − | − |
| 39 | 3+ | 3+ | 4+ | 8+ | − | + | − | − | − | − |
| 40 | 6+ | 2+ | 5+ | 3+ | + | + | − | − | + | − |
| 41 | 2+ | 1+ | 4+ | 7+ | − | + | − | + | − | − |
| 42 | 2+ | 1+ | 3+ | 5+ | − | − | − | + | − | − |

TABLE 3-continued

Measurements of IgG and IgM antibodies by Western Blot and Multi-Peptide ELISA against *Borrelia burgdorferi* antigens and peptides in patients with symptoms of Lyme disease. Possible cross-reaction with *Babesia*, *Ehrlichia* and unrelated peptides from *Treponema palidum*

| | Western Blot | | Multi-Peptide ELISA | | | | | | | |
|---|---|---|---|---|---|---|---|---|---|---|
| | | | *Borrelia* Peptides | | *Babesia* Peptides | | *Ehrlichia* Peptides | | Unrelated Peptides | |
| Sample # | IgG | IgM | IgG | IgM | IgG | IgM | IgG | IgM | IgG | IgM |
| 43 | 2+ | – | 1+ | 1+ | – | + | – | – | – | – |
| 44 | 1+ | 2+ | 6+ | 7+ | + | + | – | + | – | – |
| 45 | 2+ | 1+ | 4+ | 9+ | – | + | – | + | – | + |
| 46 | 2+ | – | 5+ | 2+ | – | – | – | – | – | – |
| 47 | 1+ | 1+ | 5+ | 7+ | + | + | – | – | – | – |
| 48 | 5+ | 4+ | 4+ | 9+ | – | + | – | + | – | + |
| 49 | 2+ | – | 1+ | – | – | – | – | – | – | – |
| 50 | 5+ | 1+ | 4+ | 7+ | + | + | – | – | – | – |
| 51 | 3+ | 1+ | 4+ | – | – | – | – | – | – | – |
| 52 | 1+ | 3+ | 4+ | 5+ | – | + | + | + | + | + |
| 53 | 6+ | 5+ | 2+ | 5+ | – | + | – | – | – | – |
| 54 | 1+ | 4+ | 3+ | 5+ | – | – | – | – | – | – |
| 55 | 4+ | 2+ | 9+ | – | + | – | – | – | – | – |
| 56 | 1+ | 5+ | 8+ | 9+ | – | + | – | – | – | – |
| 57 | 5+ | 3+ | 3+ | – | – | – | – | – | – | – |
| 58 | 5+ | 1+ | 6+ | – | – | – | – | – | – | – |
| 59 | – | 1+ | 3+ | – | – | – | – | – | – | – |
| 60 | 1+ | 1+ | 5+ | 3+ | – | + | – | – | – | – |

TABLE 4

Measurements of IgG and IgM antibodies by Western Blot and Multi-Peptide ELISA against *Borrelia burgdorferi* antigens and peptides in patients with symptoms of Lyme disease. Possible cross-reaction with *Babesia*, *Ehrlichia* and unrelated peptides from *Treponema palidum*.

| | Western Blot | | Multi-Peptide ELISA | | | | | | | |
|---|---|---|---|---|---|---|---|---|---|---|
| | | | *Borrelia* Peptides | | *Babesia* Peptides | | *Ehrlichia* Peptides | | Unrelated Peptides | |
| Sample # | IgG | IgM | IgG | IgM | IgG | IgM | IgG | IgM | IgG | IgM |
| 1 | 2+ | 3+ | 4+ | 2+ | – | – | – | – | – | – |
| 2 | 3+ | – | 5+ | 3+ | + | – | – | – | – | – |
| 3 | 5+ | 1+ | 4+ | 4+ | – | – | – | + | + | – |
| 4 | 5+ | 10+ | 8+ | 6+ | + | + | – | – | + | – |
| 5 | 5+ | 3+ | 5+ | 7+ | + | + | – | – | + | + |
| 6 | 4+ | 7+ | 3+ | 8+ | – | + | – | + | + | – |
| 7 | 2+ | 2+ | 1+ | 3+ | – | + | – | + | – | – |
| 8 | 3+ | 4+ | 2+ | 6+ | + | + | – | + | – | – |
| 9 | – | – | 3+ | 5+ | + | + | – | – | + | + |
| 10 | 4+ | 3+ | 2+ | 7+ | – | + | – | + | + | – |
| 11 | 1+ | 2+ | 1+ | 5+ | – | + | – | – | – | – |
| 12 | – | – | 2+ | 1+ | + | + | – | – | – | – |
| 13 | 2+ | 2+ | 1+ | 1+ | – | – | – | – | + | – |
| 14 | 5+ | 6+ | 2+ | 8+ | – | + | – | + | + | + |
| 15 | 5+ | 5+ | 3+ | 8+ | – | – | – | – | + | + |
| 16 | 2+ | 1+ | 3+ | 7+ | – | + | – | + | – | + |
| 17 | 5+ | – | 4+ | 1+ | – | – | – | – | + | – |
| 18 | 5+ | 1+ | 2+ | 1+ | – | + | – | – | + | – |
| 19 | 2+ | – | 4+ | 6+ | + | + | – | + | – | – |
| 20 | – | – | 1+ | 5+ | + | + | – | + | + | + |
| 21 | 3+ | 1+ | 3+ | 2+ | + | + | – | – | – | – |
| 22 | 5+ | 1+ | 2+ | 1+ | – | – | – | – | – | – |
| 23 | 1+ | – | 1+ | 3+ | – | + | – | + | – | + |
| 24 | 1+ | 1+ | 1+ | 3+ | – | – | – | – | – | – |
| 25 | 2+ | 3+ | 7+ | 9+ | + | + | – | + | – | + |
| 26 | – | 2+ | – | 9+ | – | + | – | – | – | + |
| 27 | 2+ | 3+ | 3+ | 6+ | + | – | – | – | + | + |
| 28 | – | – | – | – | – | – | – | – | – | – |
| 29 | 1+ | – | 4+ | 1+ | + | – | – | – | + | – |
| 30 | 1+ | 1+ | – | 1+ | – | – | – | – | – | – |
| 31 | 1+ | 5+ | – | 4+ | – | – | – | – | – | – |

TABLE 4-continued

Measurements of IgG and IgM antibodies by Western Blot and Multi-Peptide ELISA against *Borrelia burgdorferi* antigens and peptides in patients with symptoms of Lyme disease. Possible cross-reaction with *Babesia*, *Ehrlichia* and unrelated peptides from *Treponema palidum*.

| | Western Blot | | Multi-Peptide ELISA | | | | | | | |
| --- | --- | --- | --- | --- | --- | --- | --- | --- | --- | --- |
| | | | *Borrelia* Peptides | | *Babesia* Peptides | | *Ehrlichia* Peptides | | Unrelated Peptides | |
| Sample # | IgG | IgM | IgG | IgM | IgG | IgM | IgG | IgM | IgG | IgM |
| 32 | – | 6+ | – | 8+ | – | – | – | – | – | – |
| 33 | 2+ | 2+ | 4+ | 5+ | + | – | – | – | – | + |
| 34 | 3+ | 7+ | 3+ | 8+ | + | + | – | + | – | + |
| 35 | 2+ | 4+ | 3+ | 2+ | – | – | – | – | – | – |
| 36 | 8+ | 11+ | 9+ | 8+ | + | – | + | – | + | – |
| 37 | 2+ | 1+ | 2+ | – | + | + | – | – | + | – |
| 38 | 1+ | 2+ | 4+ | 6+ | – | + | – | – | + | – |
| 39 | – | 3+ | – | 1+ | – | – | – | – | – | + |
| 40 | 1+ | 2+ | 4+ | 3+ | – | – | – | – | + | – |
| 41 | 2+ | 4+ | 2+ | 5+ | – | – | + | + | – | + |
| 42 | – | 3+ | 1+ | 3+ | – | – | – | – | – | – |
| 43 | 1+ | 5+ | 2+ | 3+ | – | – | – | + | – | – |

EXAMPLE 2

CASE # 1

A 42-year-old man presented the following symptoms: headaches, stiffness in the neck, difficulty speaking, change in smell, blurred vision, ringing in the ears, nausea, joint pain, loss of reflexes, loss of muscle tone in the legs, shortness of breath, night sweats, diminished exercise tolerance, burning sensations in the body, weakness in thighs, pressure in head, poor balance, increased motion sickness, encephalopathy, depression, personality change (becomes quiet when in pain), anxiety and panic attacks, bipolar disorder, dementia, over-emotional, disturbed sleep.

Figure 5:
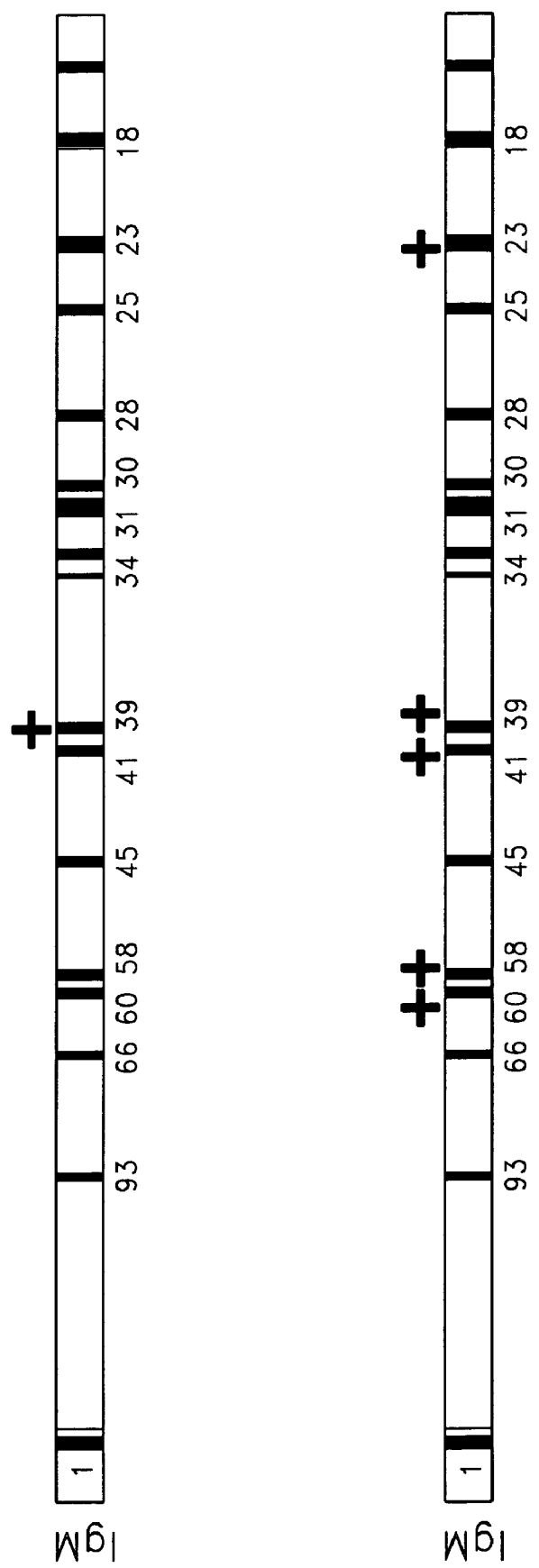
FIG. 5 shows an IgG and IgM Western blot assay for Case #1.

Based on these symptoms and abnormal SPECT scan, patient was diagnosed by a neurologist as having CNS Lyme disease. For confirmation patient was challenged with antibiotic for 3 days and PCR was performed on blood and urine, which tested positive. IgG and IgM ELISA, Western Blot and multi-peptide ELISA were performed on the serum. Results of ELISA IgG and IgM were negative (IgG 98 reference range <100, IgM 32 reference range <100). Results of the Western Blot assay shown in FIG. 5 gave positive results with 23, 39, 41, 58 and 60 kDa bands for IgG and 39 kDa band for IgM. Overall, these serological assays were interpreted as intermediate results. Subsequently, we performed the IgG and IgM multi-peptide ELISA, and the results, as presented in FIGS. 6-7, not only showed that the patient was positive for *Borrelia* lysate, OspA and OspC and B. *sensu stricto* IgG, but was highly positive for *Babesia* IgG as well.

Figure 8A:
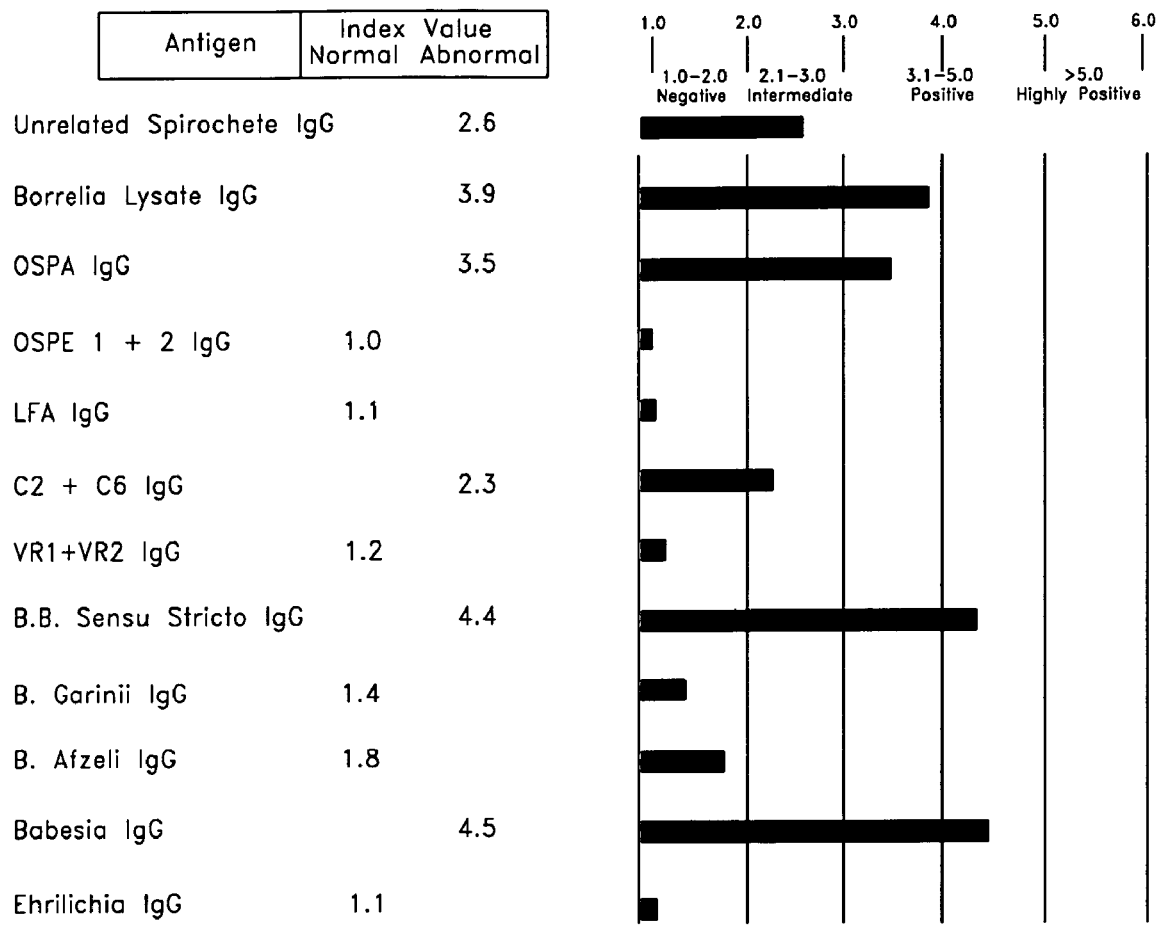
FIG. 8 shows a chart of index values of IgG and IgM antibodies against 12 different peptides and antigens from Case #1.
Figure 8B:
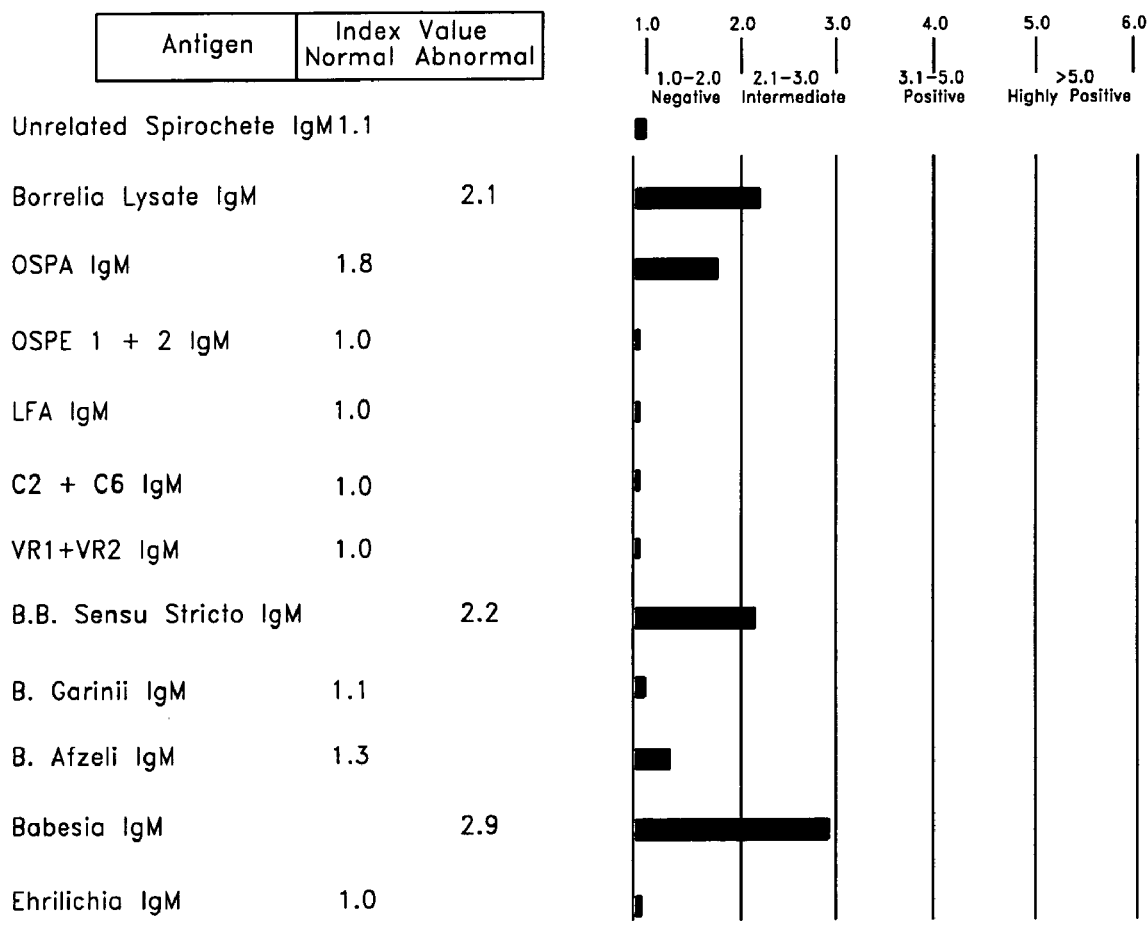

The optical densities of Case #1 were divided by 2 standard deviations above the mean values of negative control, and the converted index values are reported in FIGS. 8A and 8B.

Conclusion:

Patient negative for IgG and IgM by ELISA but intermediate by Western Blot assay could be confirmed by multi-peptide ELISA for Lyme disease.

EXAMPLE 3

CASE # 2

Figure 9:
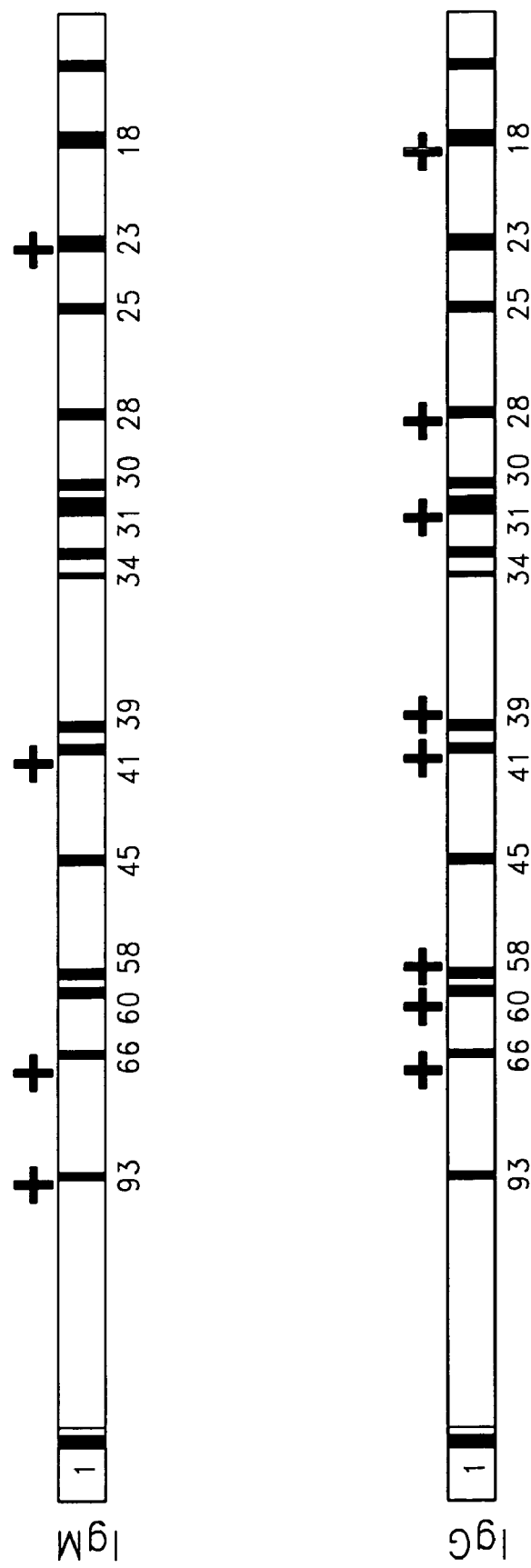
FIG. 9 shows an IgG and IgM Western blot assay for Case #2.

A 45-year-old woman presented the following symptoms: mental fatigue, difficulty focusing, blurred vision, inability to find words, difficulty recognizing people, joint and muscular pain, ringing in the ear, increased headaches, deep tendon pain, deep hip pain, erythemic rash noted on left shoulder blade. A brain SPECT scan showed mild to moderate area of patchy cortical activity involving the frontal lobe, particularly on the right superiorly and the right anteriorly. A neurologist specializing in Lyme disease concluded that the findings might be consistent with vasculitis as well as borreliosis. IgG and IgM ELISA, Western Blot and multi-peptide ELISA were performed on the serum. Results of IgG and IgM by ELISA were positive (IgG 220, IgM 280 reference range <100). Results of Western Blot, as shown in FIG. 9, gave positive results with 18, 28, 31, 39, 41, 58, 60 and 66 kDa bands for IgG, and 23, 41, 66 and 93 kDa for IgM. These serological assays were interpreted as positive results. For further confirmation we performed the IgG and IgM multi-peptide ELISA, and results presented in FIGS. 10-11 show clear elevation in both IgG and IgM not only against *Borrelia* lysates but against several peptides.

Figure 12A:
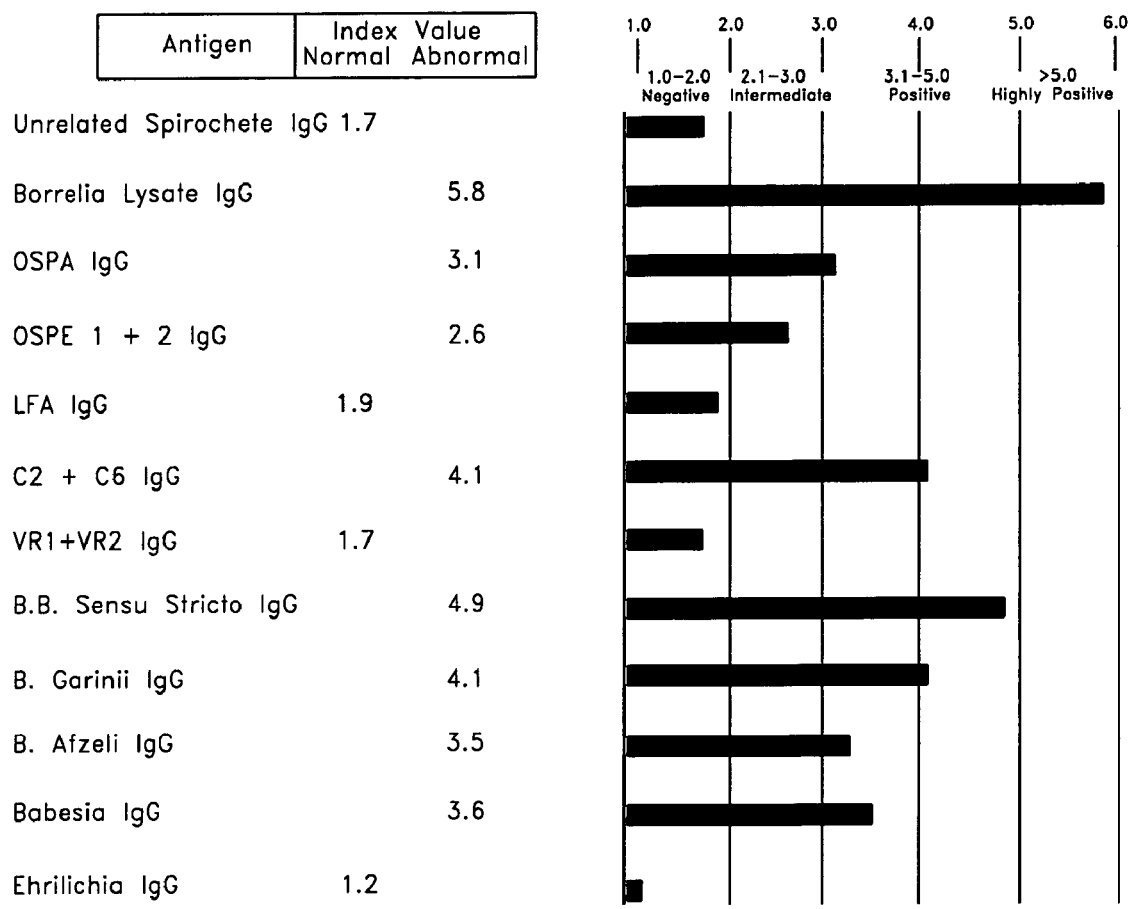
FIG. 12 shows a chart of index values of IgG and IgM antibodies against 12 different peptides and antigens from Case #2.
Figure 12B:
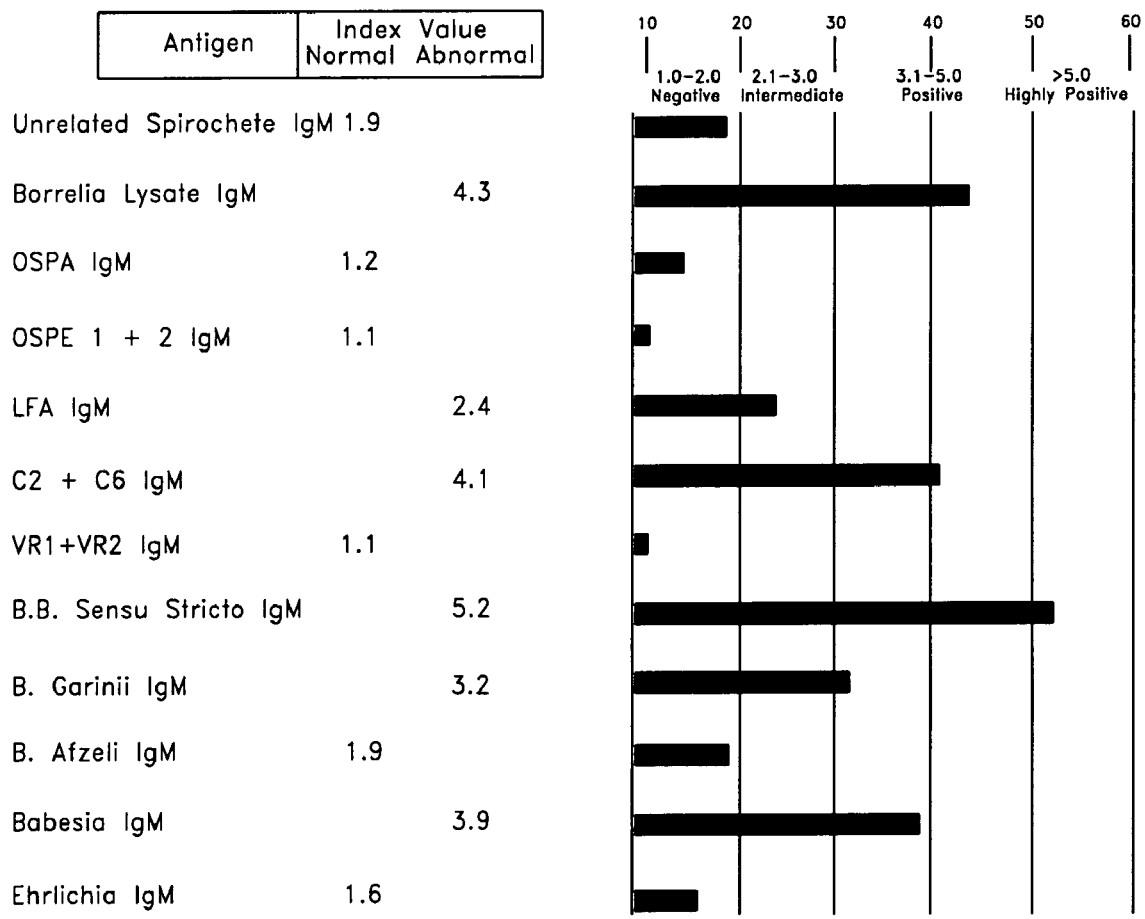

The optical densities of Case #2 were divided by 2 standard deviations above the mean values of negative control, and the converted index values are reported in FIGS. 12A and 12B.

Conclusion:

All three assays, ELISA, Western Blot, and multi-peptide ELISA are in agreement for the presence of IgG and IgM antibodies that confirm the diagnosis of Lyme disease.

EXAMPLE 4

CASE # 3

Figure 13:
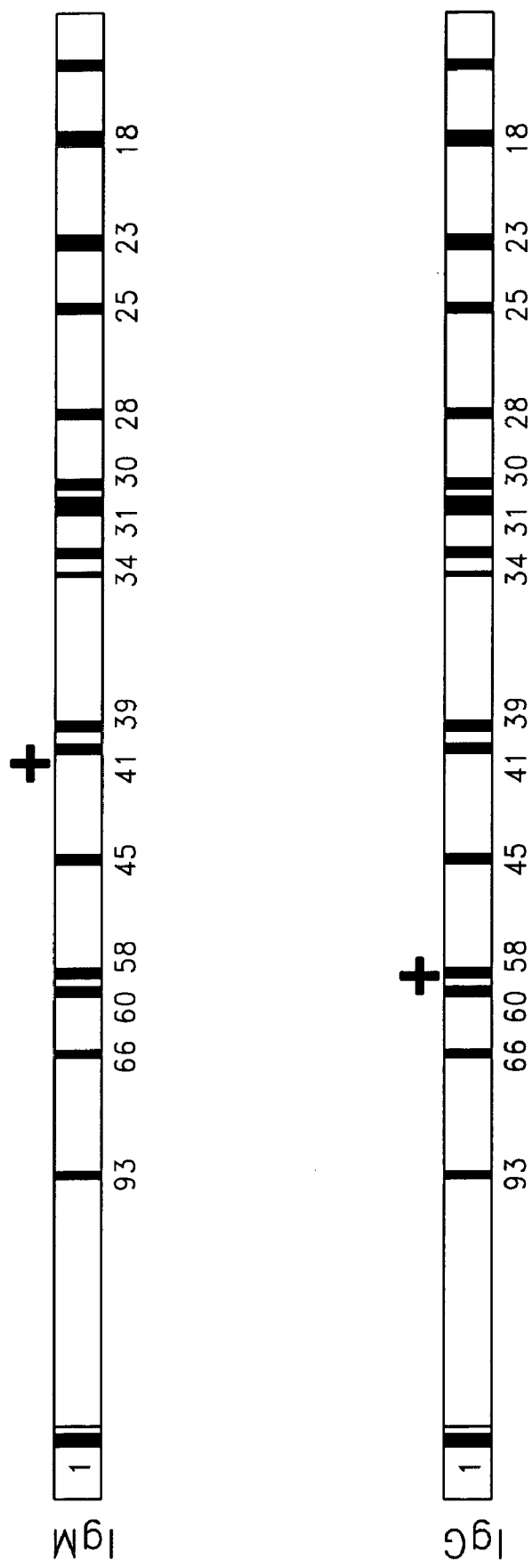
FIG. 13 shows an IgG and IgM Western blot assay for Case #3.

A 36-year-old man had episodes of Lyme bites with *Erythema migrans* on his arms. His symptoms were fatigue, falling asleep during the day, and numbness in the arms and legs. He was put on anti-psychotic agents, which made his situation worse. When he was put on antibiotics his symptoms improved. A Brain SPECT scan was performed and abnormalities in the frontal lobe were observed. He was tested by ELISA and Western Blot assays. While ELISA was positive for IgG (160) and for IgM (195), Western Blot gave positive results only with 58 kDa for IgG and 41 kDa for IgM (FIG. 13). Since these results were borderline positive and did not confirm diagnosis of Lyme disease, the multi-peptide ELISA was performed. These results are presented in FIGS. 14-15 and show clear elevation of IgG and IgM antibodies against different subspecies of *Borrelia* (*B. garinii*), but IgM antibodies were highly positive against *Babesia*, as well. These results may indicate infections with multiple organisms in the same individual.

Figure 16A:
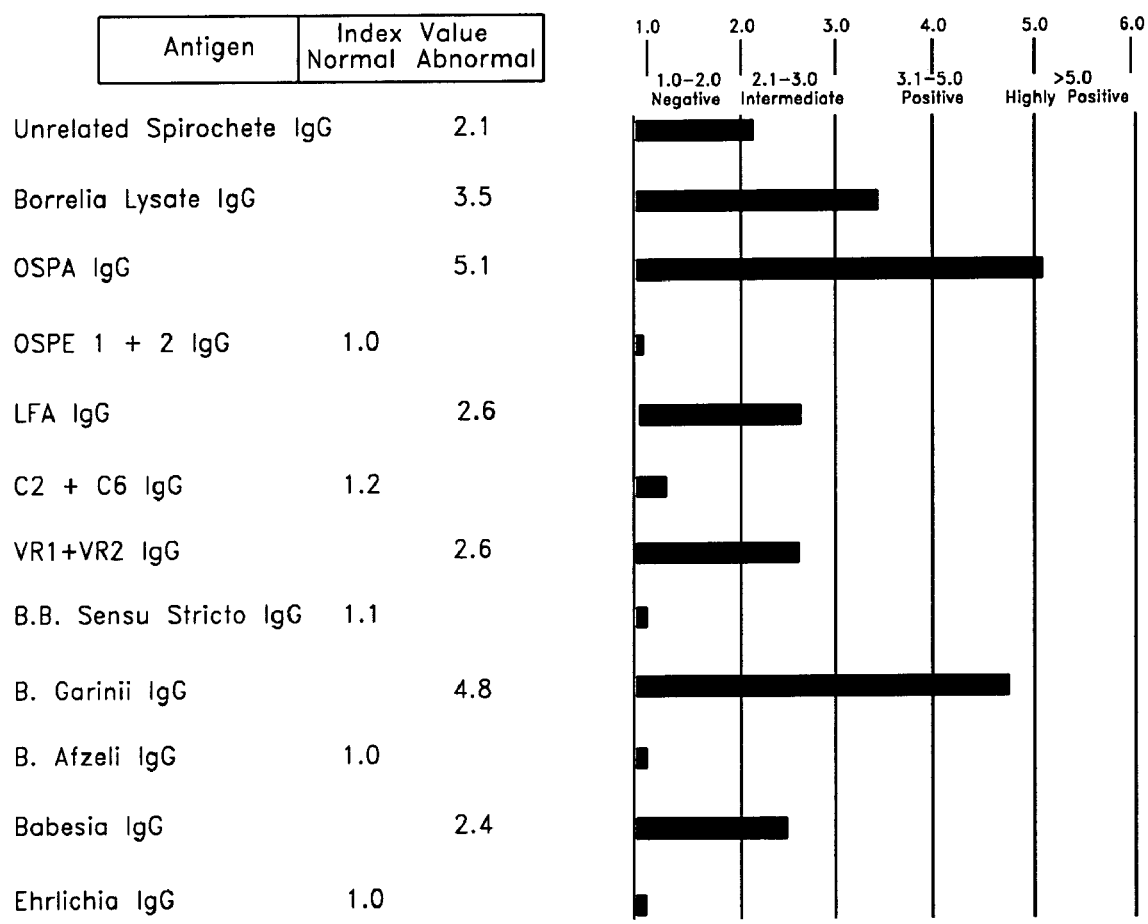
FIG. 16 shows a chart of index values of IgG and IgM antibodies against 12 different peptides and antigens from Case #3.
Figure 16B:
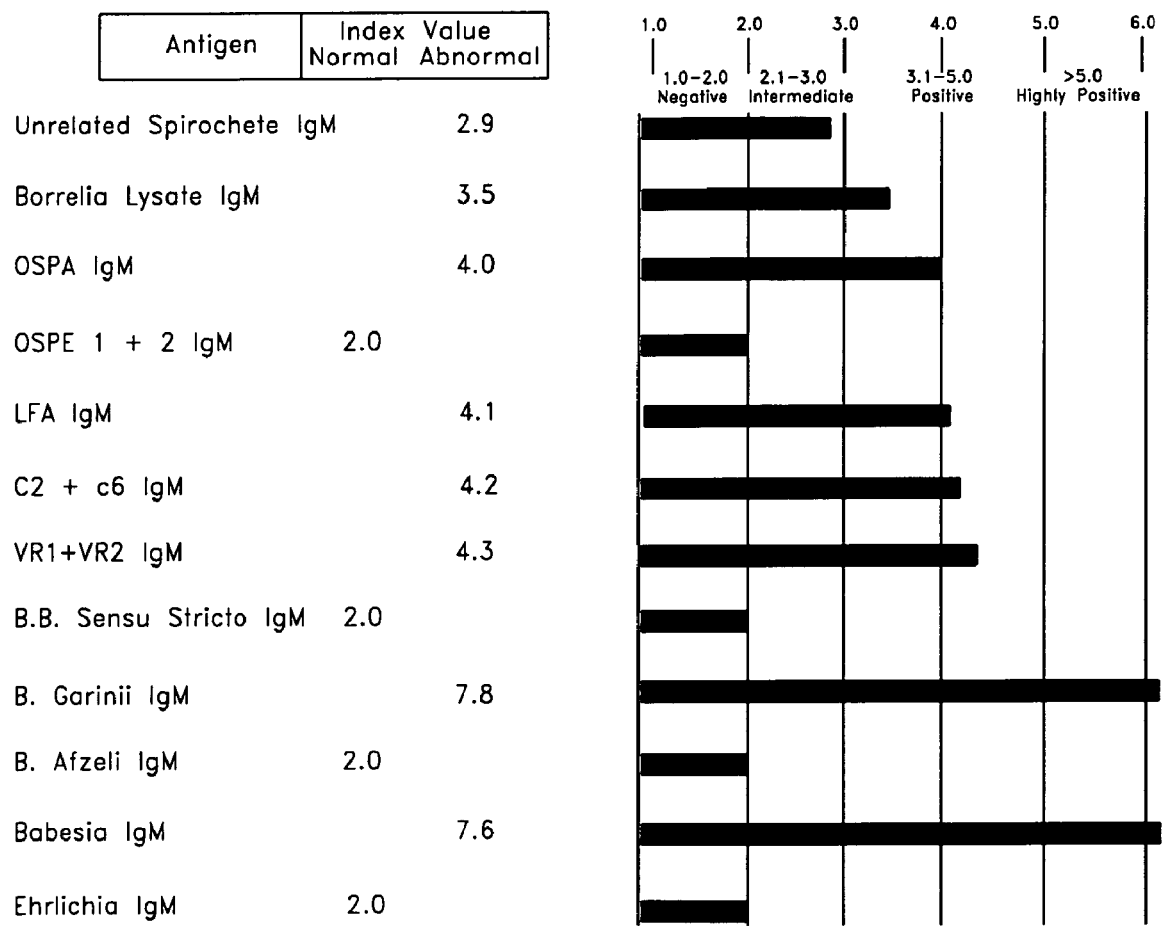

The optical densities of Case #3 were divided by 2 standard deviations above the mean values of negative control, and the converted index values are reported in FIGS. 16A and 16B.

Conclusion:

The highest levels of antibodies were detected against different subspecies of *Borrelia* (*B. garinii*) and *Babesia* peptides. These results indicate that infection with different subspecies of *Borrelia* may give a false negative by Western Blot, and that infection with multiple organisms (*Borrelia* and *Babesia*) is possible.

EXAMPLE 5

CASE # 4

Figure 17:
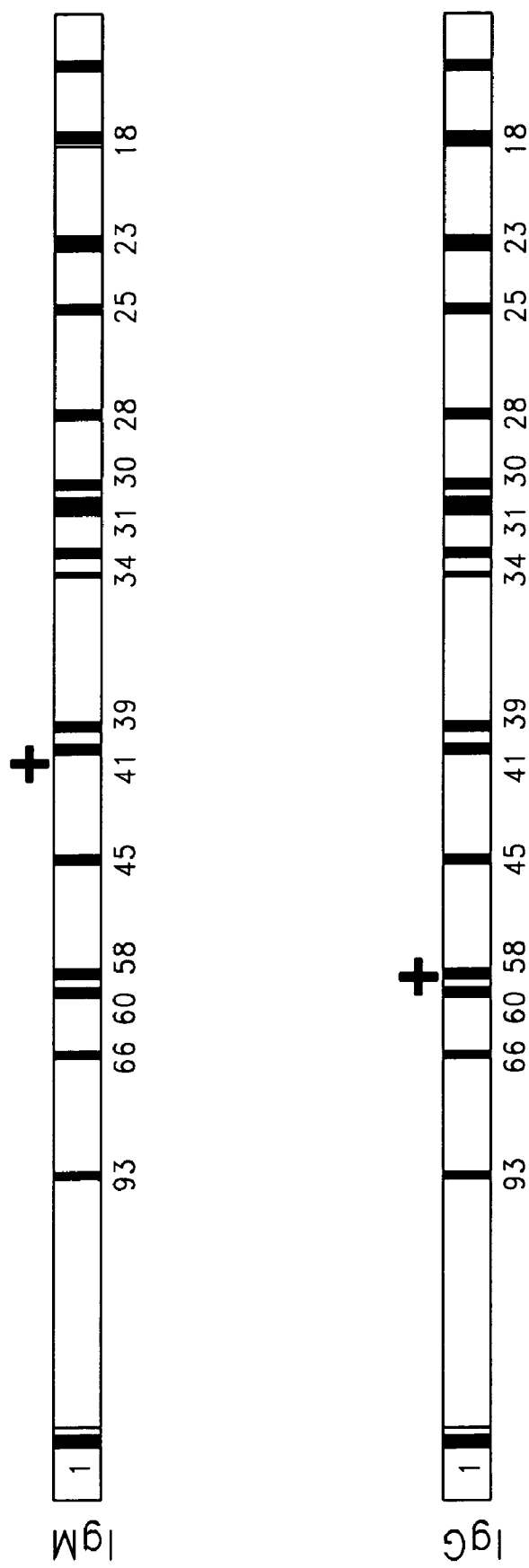
FIG. 17 shows an IgG and IgM Western blot assay for Case #4.

A 47-year-old man was presented with the following symptoms, beginning in 1996: extreme fatigue, muscle and joint pain, shin splints, memory and concentration loss, testicular pain, eye problems, sexual dysfunction, numbness, anxiety and depression (frequent anxiety attacks), anger. History included tonsillitis, appendicitis, umbilical hernia, vasectomy, malaria, wrist/arm/elbow/collar bone/shoulder surgery, aneurysms behind knees, ulcers, concussions, eczema. Psoriasis. Patient had to stay in bed for 18 months. For exclusion of possible Lyme disease ELISA and Western Blot was performed. Results of IgG and IgM by ELISA were negative (<50 ELISA units). IgG and IgM Western Blot assay revealed a band at 58 kDa for IgG and a band at 41 kDa for IgM, as shown in FIG. 17. Based on these results patient was classified as intermediate for Lyme disease and was treated with IV and oral antibiotics, which did not have any effect on the symptoms. We performed the IgG and IgM multi-peptide ELISA, and the results (FIGS. 18-19) were negative. Further laboratory testing was performed and based on positive results for Epstein-Barr virus and Herpes Type 6 IgG and IgM. Patient was diagnosed with chronic fatigue and fibromyalgia.

Figure 20A:
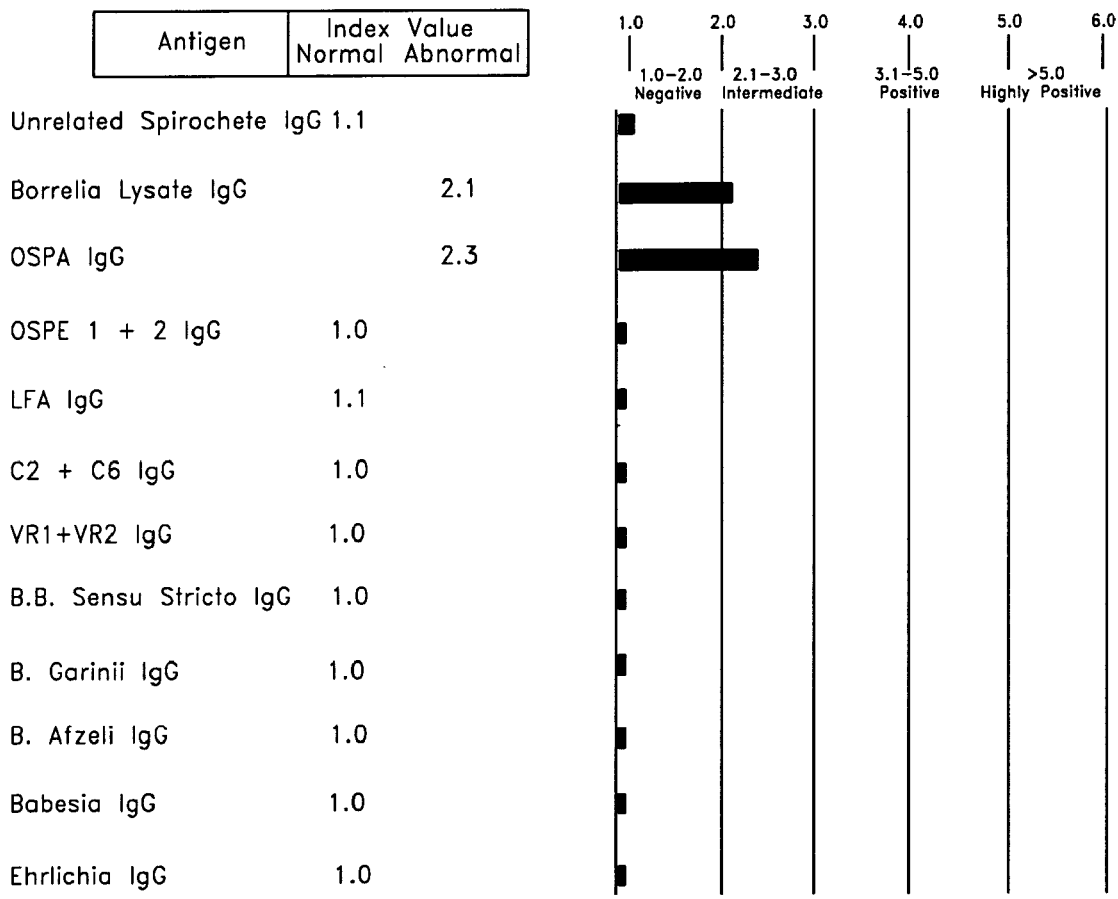
FIG. 20 shows a chart of index values of IgG and IgM antibodies against 12 different peptides and antigens from Case #4.
Figure 20B:
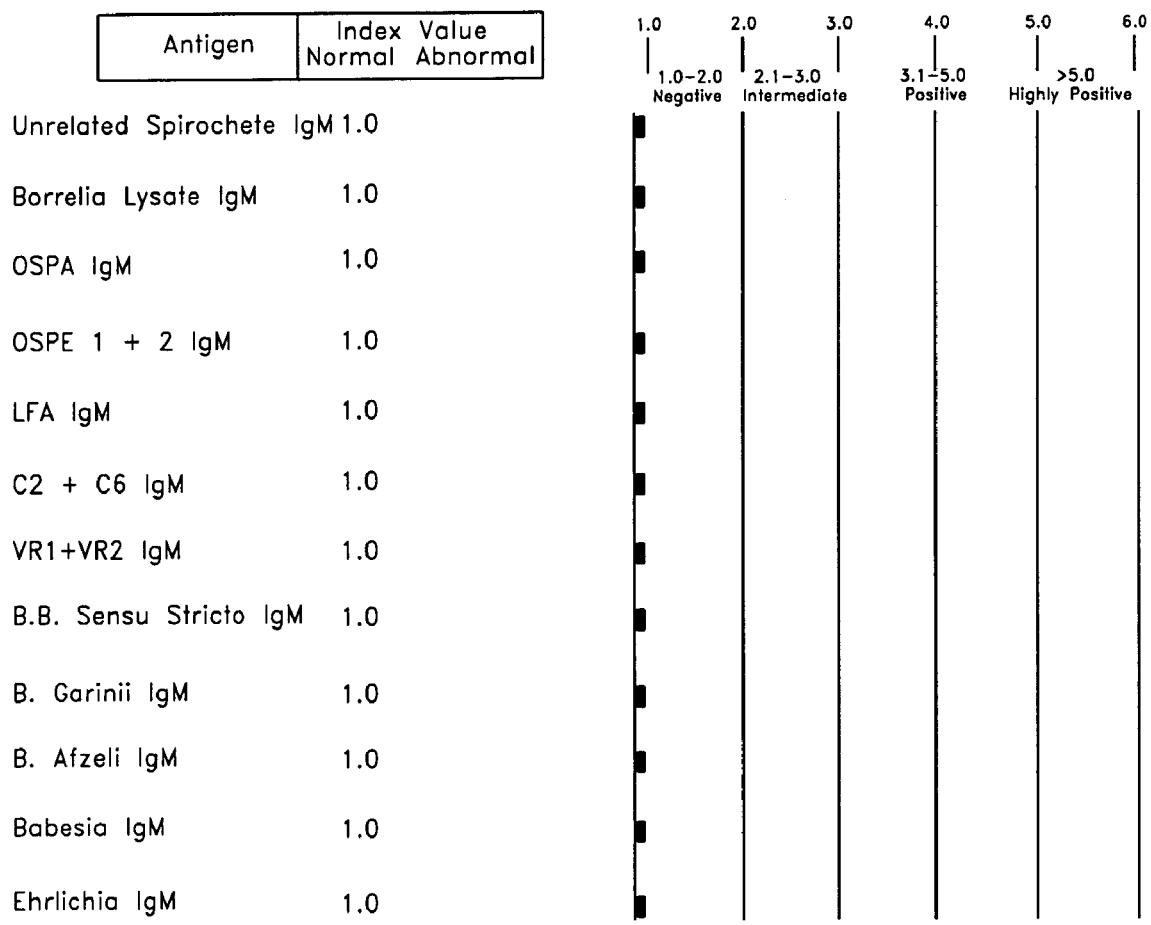

The optical densities of Case #4 were divided by 2 standard deviations above the mean values of negative control, and the converted index values are reported in FIGS. 20A and 20B.

Conclusion:

Serum from patients with chronic fatigue and fibromyalgia and high titers of IgG and IgM against EBV and Herpes Type 6 may react with different bands of *Borrelia* antigen and give false positive results by Western Blot. These false positive results by Western Blot were confirmed by multi-peptide ELISA, and Lyme disease was excluded in Case #4.

EXAMPLE 6

CASE # 5

A 16-year-old girl presents with a history of fever and rash. The mother reports that she had been playing outside the previous week, and tick bites had been observed on the child.

Figure 21:
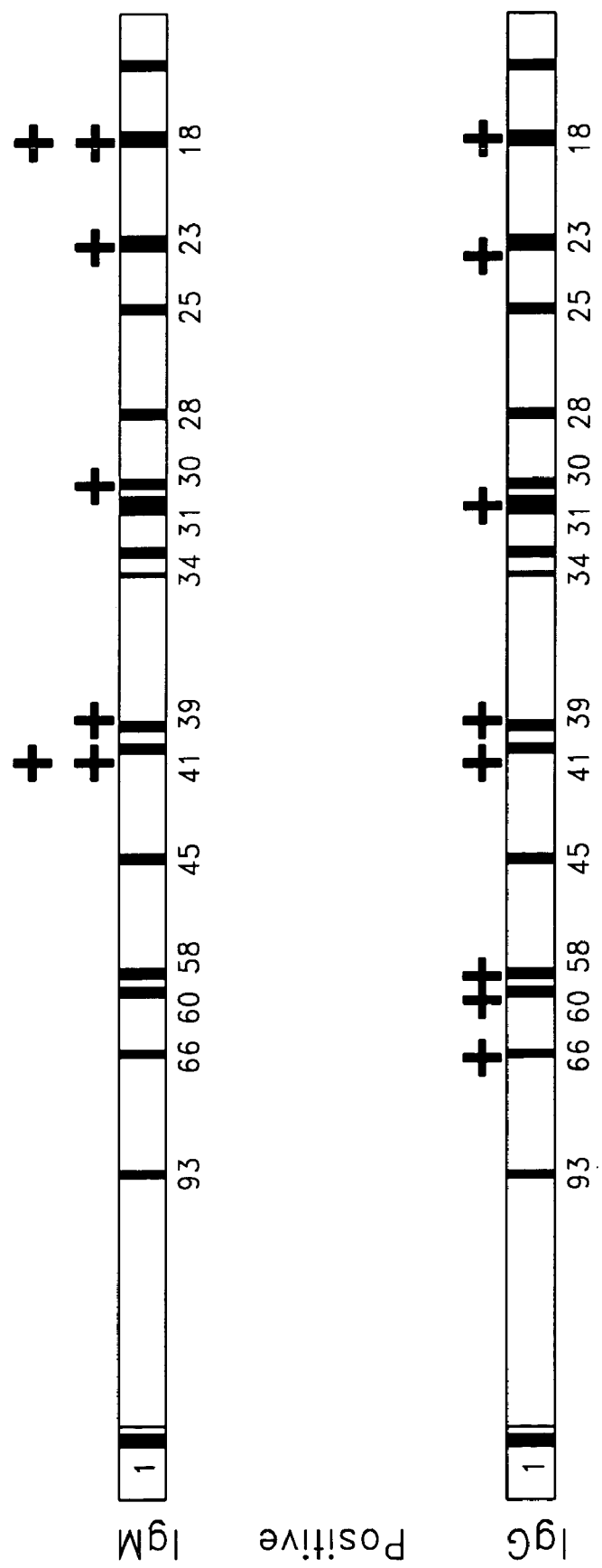
FIG. 21 shows an IgG and IgM Western blot assay for Case #5.

Based on laboratory test results, including ELISA IgG of 150, IgM of 380, and Western Blot with positive bands of 18, 23, 31, 39,41, 58, 60, 68 kDa for IgG, and positive bands of 18, 23, 30, 39 and 41 kDa for IgM (FIG. 21), patient was diagnosed with Lyme disease and treatment with antibiotics commenced immediately. In addition multi-peptide ELISA was performed. Results presented in FIGS. 22-23 showed clear elevation in IgG and IgM antibodies not only against 8-9 different peptides but against *Babesia* and *Ehrlichia*. These results may indicate infection with multiple organisms in the same individual.

Figure 24A:
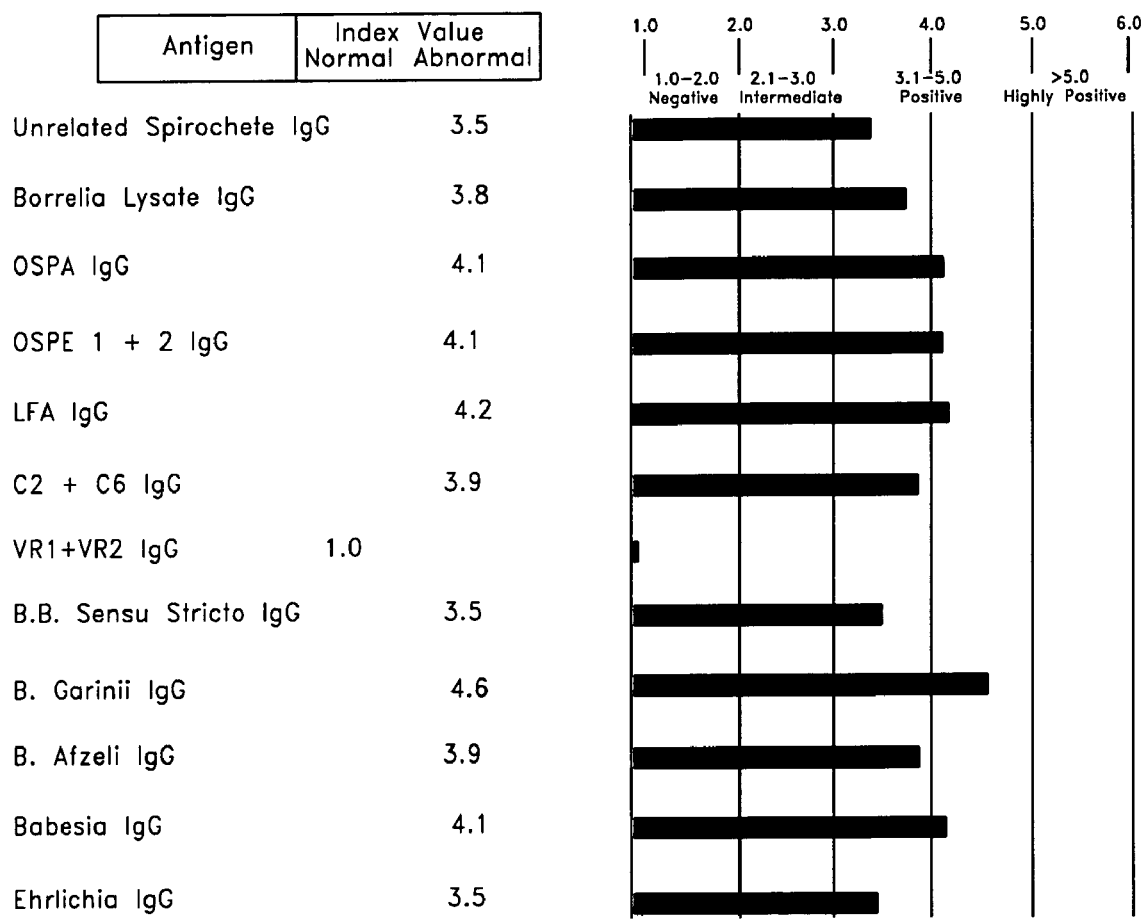
FIG. 24 shows a chart of index values of IgG and IgM antibodies against 12 different peptides and antigens from Case #5.
Figure 24B:
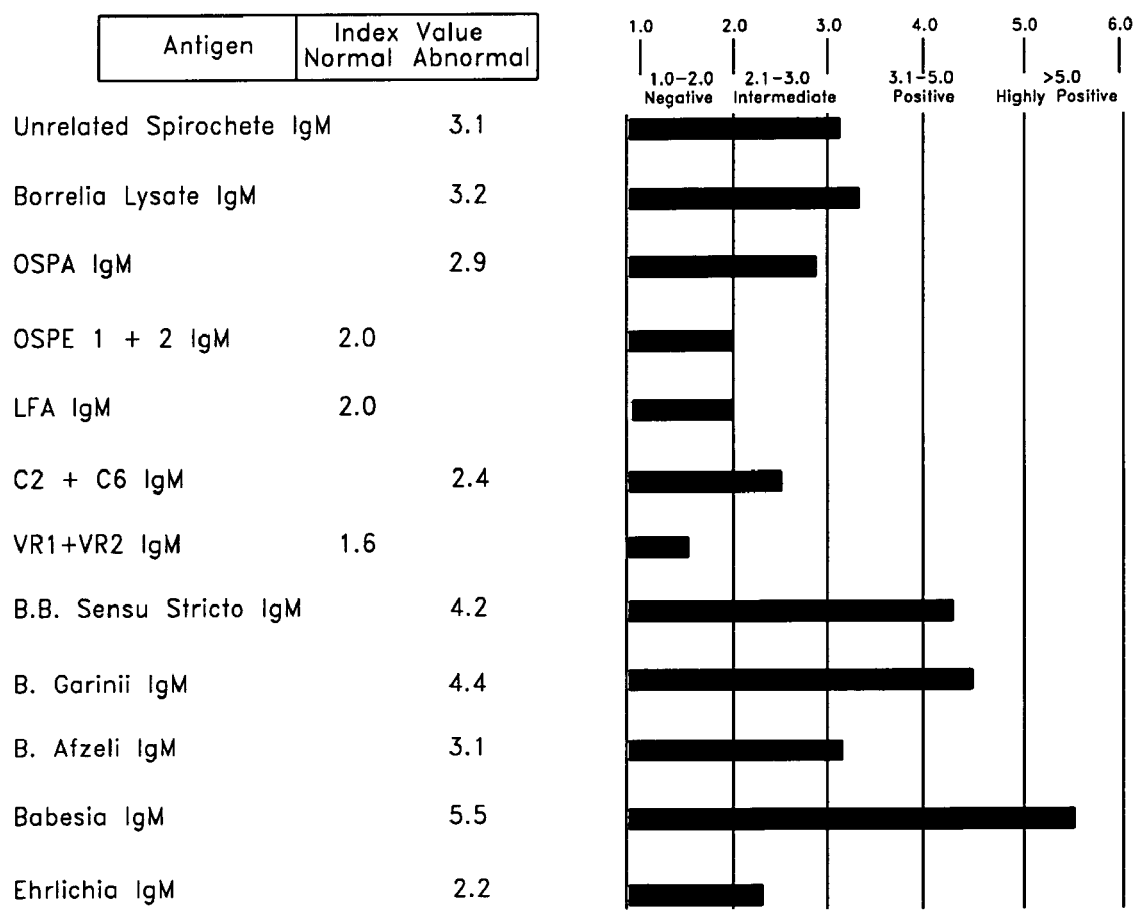

The optical densities of Case #5 were divided by 2 standard deviations above the mean values of negative control, and the converted index values are reported in FIGS. 24A and 24B.

Conclusion:

Results of multi-peptide ELISA are in agreement with ELISA and Western Blot IgG and IgM. However, the multi-peptide ELISA is identifying the subspecies patient was infected with as *B. garinii* and not *B. b. sensu stricto*. The multi-peptide ELSIA indicates that in addition to *B. garinii*, and based on very high levels of IgM antibodies against *Babesia* peptide, multiple infections with *Borrelia* and *Babesia* are a possibility. Finally, since these antibodies reacted with unrelated peptides (*Treponema palidum*), then some of these antibodies may be cross-reactive.

Kits

As a matter of convenience, the assay method of the preferred embodiments can be provided in the form of a kit. Such a kit is a packaged combination including a basic element of at least one peptide of infective agents selected from the group consisting of *Borrelia, Babesia*, and *Ehrlichia*, corresponding recombinant antigens, or synthetic peptides.

(a) Peptides of Borrelia

Preferably, *Borrelia* is *Borrelia burgdorferi*. Preferably, the *Borrelia* peptides are from different components during different life cycles. Preferably, the *Borrelia* peptides are selected from the group consisting of outer surface protein A, outer surface protein C, outer surface protein E, leukocyte function associated antigen, immunodominant proteins, variable major proteins, and Decorin-binding protein from *Borrelia* species. Preferably, the *Borrelia* peptides are selected from the group consisting of SEQ ID NOS:1-11.

(b) Peptides of *Babesia*

Preferably, the *Babesia* peptides are selected from the group consisting of *Babesia microti, Babesia bovis*, and *Babesia equi*. Preferably, the *Babesia* peptides are selected from the group consisting of SEQ ID NOS: 12-14.

(c) Peptides of *Ehrlichi*

Preferably, the *Ehrlichia* peptides are selected from the group consisting of *Anaplasma marginale* and *Anaplasma ovis*. Preferably, the *Ehrlichia* peptides are selected from the group consisting of SEQ ID NOS:15-16.

A preferred kit can further comprise standards, negative controls, positive controls, substrate, and an immunoassay selected from the group consisting of ELISA test, dot blot, and multi-peptide ELISA Blot. A preferred can further comprise a component selected from the group consisting of nitrocellulose paper, plastics or combs, directions for preparation of specimens and serum diluents, wash buffers, and substrate buffers.

Many modifications and variations of the embodiments described herein may be made without departing from the scope, as is apparent to those skilled in the art. The specific embodiments described herein are offered by way of example only.

REFERENCES

1. Steere, A. C., Malawista, S. E., Syndman, D. R., Shope, R. E., Andiman, W. A., Ross, M. R., Steele, F. M. An epidemic of oligoarticular arthritis in children and adults in three Connecticut communities. Arthritis and Rheumatism 20:7-17, 1977.
2. Steere, A. C., Gibofsky, A., Patarroyo, M. E., Winchester, R., Hardin, J. A. and Malawista, E. Lyme arthritis: clinical and immunogenetic differentiation from rheumatoid arthritis. Ann. Intern. Med. 90:896-901, 1979.
3. Steere, A. C., Grodzicki, R. L., Kornblatt, A. N., Craft, J. E., Barbour, A. G., Burgdorfer, W., Schmid, G. P., Johnson, E. and Malawista, S.E. The spirochetal etiology of Lyme disease. N. Engl. J. Med. 308:733-740, 1983.
4. Stanek, G., Pletschette, M., Flamm, H., Hirschl, A. M., Aberer, E., Kristoferitsch, W. and Schmutzhard, E. European Lyme borreliosis, p. 274-282. In J. L. Benach and E. M. Bosler (ed.), Lyme disease and related disorders. The New York Academy of Sciences, New York, N.Y., 1988.
5. Steere, A. C. Lyme disease. N. Engl. J. Med. 321:586-596, 1989.
6. Steere, A. C., Taylor, E., McHugh, G. L. and Logigian, E. L. The overdiagnosis of Lyme disease. JAMA 269:1812-1816, 1993.
7. Kantor, F. S. Disarming Lyme disease. Scientific American 271:34-39, 1994.
8. Romano, V., Costa, K., Hustad, S. and Mulligan, T. Lyme disease in California. Booklet published by California Mosquito and Vector Control, 1992.
9. Hedberg, C. W. and Osterholm, M. T. Serologic tests for antibody to *Borrelia Burgdorferi*: another Pandora's box for medicine? Arch. Intern. Med. 150:732-733, 1990.
10. Hedberg, C. W., Osterholm, M. T., MacDonald, K. L. and White, K. E. an interlaboratory study of antibody to *Borrelia burgdorferi*. J. Infect. Dis. 155:1325-1327, 1987.
11. Jones, J. M. Serodianosis of Lyme Disease. Ann Intern. Med, 114:1064, 1991.
12. Lane, R. S., Lennette, E. T. and Madigan, J. E. Interlaboratory and intralaboratory comparison of indirect immunofluorescence assays for serodiagnosis of Lyme disease. J. Clin. Microbiol. 28:1774-1779, 1990.
13. Luger, S. W. and Krauss, E. Serologic tests for Lyme disease: interlaboratory variability. Arch. Intern. Med. 150: 761-816. 1990.
14. Schwartz, B. S., Goldstein, M. D., Ribeiro, J. M. C., Schulze, T. L. and Shahied, S. I. Antibody testing in Lyme disease: a comparison of results in four laboratories. JAMA 262:3431-3434, 1989.
15. Cooper, J. D. and Schoen, R. T. Lyme disease: difficulties in diagnosis. Infect Med. 11:509-514, 1994.
16. Craft, J. E., Grodzicki, R. L. and Steere, A. C. Antibody response in Lyme disease: evaluation of tests. J. Infect. Dis. 49:789-795, 1984.
17. Asbrink, E. and Hovmark, A. Successful cultivation of spirochetes from skin lesions of patients with *erythema chronicum migrans afzelius* and *acrodermatis chronica astrophicans*. Acta Pathol. Microbiol. Scand. 93:161-163, 1985.
18. Karlsson, M., Hovind-Hougen, K., Svenungsson, B. and Stiemstedt, G. Cultivation and characterization of spirochetes from cerebrospinal fluid of patients with Lyme borreliosis. J. Clin. Microbiol. 28:473-479, 1990.
19. Brunet, L., Spielman, A. and Telford, S. R. III. Short report: density of Lyme disease spirochetes within deer ticks collected from zoonotic sites. Am. J. Trop. Med. Hyg. 53:300-302, 1995.
20. Goodman, J. A. Nucleic acid detection of Borrelia *burgdorferi infection*., p.127-135. In P. K. Coyle (ed.). Lyme Disease. Mosby-Year Book Inc., St. Louis, Mo., 1993.
21. Goodman, J. L., Bradley, J. F., Ross, A. E., Goellner, P., Lagus, A., Vitale, B., Berger, B. W., Luger, S. W. and Johnson R. C. Bloodstream invasion in early Lyme Disease: results from a prospective, controlled, blinded study using the polymerase chain reaction. Am.J.Med. 99:6-12.1995.
22. Goodman, J. L., Jurkovich, P., Kramber, J. M. and Johnson, R. C>Molecular detection of persistent *Borrelia burgdorferi* in the urine of patients with active Lyme disease. Infect. Immun. 59:269-278. 1991.
23. Dressler, F., Whalen, J. A., Reinhardt, B. N. and Steere, A. C. Western blotting in the serodiagnosis of Lyme disease. J. Infect. Dis. 167:392-400, 1993.
24. Engstrom, S. M., E. Shoop, and R. C. Johnson. Immunoblot interpretation criteria for serodiagnosis of early Lyme disease. J. Clin Microbiol 33:419-427, 1995.
25. Gilmore, R. D., Kappel, K. J., Johnson, B. J. B. Molecular characterization of a 35 kilodalton protein of *Borrelia Burgdorferi*, an antigen of diagnostic importance in early Lyme disease. J. Clin. Microbiol. 35:86-91, 1997.
26. Sung, S. Y., J. McDowell, J. A Carlyon, and R. T. Marconi. Mutation and combination in the upstream homology box flanked OspE related genes of the Lyme disease spirochetes results in the development of new antigenic variants during infection. Infect. Immun. 68:1319-1327,2000.
27. Sung, S. Y., J. V. McDowell, and R. T. Marconi. Evidence for the contribution of point mutations to VlsE variation and for apparent constraints on the net accumulation of sequence changes in VlsE during infection with the Lyme disease spirochetes. J. Bacteriol 168:5855-5861, 2001.
28. Zhang, J. R. and S. J. Norris. Genetic variation of the *Borrelia Burgdorferi* gene VlsE involves cassette specific, segmental gene conversion. Infect. Immun. 66:3698-3704.
29. McDowell, J. V., Sung S., Hu, L. T. Evidence that the variable regions of the central domain of VlsE are antigenic during infection with Lyme disease spirochetes infection and immunity. 70:4196-4203.
30. Ling, F. T., Alvarez, A. L., Guy et al., An immunodominant conserved region within the variable domain of VlsE, the variable surface antigen of *Borrelia burgdorferi*. J. immunology. 163:5566-5573,1999.
31. Magnarelli, L. A., J. W. Ijdo, S. J. Padula, R. A. Flavell, and E. Fikrig. 2000. Serologic diagnosis of Lyme borreliosis by using enzyme-linked immunosorbent assays with recombinant antigens. J. Clin. Microbiol. 38:1735-1739.
32. Kraiczy, P., C. Skerka, and P. F. Zipfel. 2001. Further characterization of complement regulator-acquiring surface proteins of *Borrelia burgdorferi*. Infect. Immun. 69:7800-7809.
33. Alitalo, A., T. Meri, H. Lankinen, I. Seppala, P. Lahdenne, P. S. Hefty, D. Akins, and S. Meri. 2002. Complement inhibitor factor H binding to Lyme disease spirochetes is mediated by inducible expression of multiple plasmid encoded outer surface protein E paralogs. J. Immunol. 169-3847-3853.
34. Hefty, P. S., S. E. Jolliff, M. J. Caimano, S. K. Wikel, and D. R. Atkins 2002. Changes in temporal and spatial patterns of outer surface lipoprotein expression generate population heterogencity and antigenic diversity in the Lyme disease spirochete *Borrelia burgdorferi*. Infect. Immun 70:3468-3478.

35. Metts, M. S., McDowell, J. V., Theisen, M., etal. Analysis of the OspE determinants involved in binding of Factor H and OspE targeting antibodies illicited during *Borrelia burgdorferi* infection in mice. Infection and Immunity 71:3587-3596, 2003.

36. Gross, D. M., Forsthubert, Tary-Lehmann, M. etal. Identification of LFA-1 as a candidate autoantigen in treatment resistant Lyme arthritis. Science 281:703-705, 1998.

37. McDowell, J. V., Wolfgang, J., Trane, etal. Comprehensive analysis of the Factor H binding capabilities of *Borrelia* species associated with Lyme disease: delineation of two distinct classes of Factor H. binding proteins. Infection and Immunity 71:3597-3602, 2003.

38. Roberts, D., M. Caimano, J. McDowell, M. Thiesen, A. Holm, S. Alban, E.Orff, D. Nelson, S. Wikel, J. Radolf, and R. Marconi. Environmental regulation and differential expression of members of the Bdr protein family of *Borrelia burgdorferi*. Infect. Immun. 70:7033-7041, 2002.

39. Schwan, T. G., J. Piesman. W. T. Golde, M. C. Dolan, and P. A. Rosa. 1995. Induction of an outer surface protein on *Borrelia burgdorferi* during tick feeding. Proc. Natl. Acad. Sci. USA 92:2909-2913.

40. Montgomery, R. R., S. E. Malawista, K. J. M. Feen, and L. K. Bockenstedt. 1996. Direct demonstration of antigenic substitution of *Borrelia Burgdorferi* ex vivo: exploration of the paradox of the early immune response to outer surface proteins A and C in Lyme disease. J. Exp. Med. 183:261-269.

41. Leuba-Garcia, S., R. Martinez and L. Gem. 1998. Expression of outer surface proteins A and C of *Borrelia afzeliii* in *Ixodes ricinus* ticks and in the skin of mice. Zentbl. Bakteriol. 287:475-484.

42. Feng, S., E. Hodzic, B. Stevenson and S. W. Barthold. 1998. Humoral immunity to *Borrelia burgdorferi* N40 decorin binding proteins during infection of laboratory mice. Infect. Immun. 66:2827-2835.

43. Cassatt, D. R., N. K. Patel, N. D. Ulbrandt, and M. S.Hanson. 1998. DbpA but not OspA is expressed by *Borrelia Burgdorferi* during spirochetemia and is a target for protective antibodies. Infect. Immun. 66:5379-5387.

44. Schwan, T. G., and J. Piesman 2000. Temporal changes in outer surface proteins A and C of the Lyme disease-associated spirochete, *Borrelia burgdorferi*, during the chain of infection in ticks and mice. J. Clin. Microbiol. 38:382-388.

45. Heikkila, T., Seppala, I., Saxen, H., etal. Species specific serodiagnosis of Lyme arthritis and Neuroborreliosis due to *Borrelia burgdorferi stricto*, *B. afzelli*, and *B. garinii* by using Decorin binding protein A. J. Clin. Microbiol. 40:453-460, 2002.

46. Hagman, K. E., P. Lahdenne, G. Popova, S. F. Porcella, D. R. Akins, J. D. Radolf, and M. V. Norgard. 1998. Decorin binding protein of *Borrelia burgdorferi* is encoded within a two gene operon and is protective in the murine model of Lyme borreliosis. Infect. Immun. 66:2674-2683.

47. Hanson, M. S., D. R. Cassat, B. P. Guo, N. K. Patel, M. P. McCarthy, D. W. Dorward, and M. Hook. 1998. Active and passive immunity against *Borrelia burgdorferi* decorin binding protein A (DbpA) protects against infection. Infect. Immun. 66:2143-2153

48. Fingerle, V., Rauser, S., Hammer, B., etal. Dynamics of Dissemination and outer surface protein expression of different European *Borrelia burgdorferi* sensu lato strains in artificially infected *Ixodes Ricinus Nymphs*. J.Clin. Microbiol. 40:1456-1463, 2002

49. Homer, M. J., Lodes, M. J., Reynolds, L. D., Zhang, Y., Douglass, J. F., et al. Identification and characterization of putative secreted antigens from *Babesia microti*. J. Clin. Microbiol. 41:723-729, 2003.

50. Bose, R., and B. Peymann. Diagnosis of *Babesia caballi* infections in horses by enzyme linked immunosorbent assay (ELISA) and Western blot. Int. J. Parasitol. 24:341-346. 1994.

51. Ikadai, H., X. Xuan, I. Igarashi, T Kanemaru, H. Nagasawa, K. Fujisaki, N. Suzuki, and T. Mikami. Cloning and expression of a 48 kilodalton *Babesia caballi* merozoite rhoptry protein and potential use of the recombinant antigen in an enzyme linked immunosorbent assay. J. Clin. Microbiol. 37:3475-3480. 1999.

52. Hirata, H., H. Ikadai, N. Yokoyama, X Xuan, K. Fujisaki, N. Suzuki, T. Mikami, and I. Igarashi. Cloning of a truncated *Babesia equi* gene encoding an 82 kilodalton protein and its potential use in an enzyme linked immunosorbent assay. J. Clin. Microbiol. 40:1470-1474.2002.

53. Hirata, H., X. Xuan, N. Yokoyama, Y. Nishikawa, K. Fujisaki, N. Suzuki, and I. Igarashi. Identification of a specific antigenic region of the P82 protein of *Babesia equi* and its potential use in serodiagnosis. J. Clin. Microbiol. 41:547-551. 2003.

54. Cunha, C. W., Kappmeyer L. S., McGuire T. C., etal. Conformational dependence and conservation of an immunodominant epitope within the *Babesia Equi* erythrocyte stage surface protein equi merozoite antigen 1. Clin Diag. Lab. Immunol 9:1301-1306, 2002.

55. Tamaki, Y., Hirata, H., Takabatake, N., et al. Molecular cloning of a *Babesia Caballi* gene encoding the 134 kilodalton protein and evaluation of its diagnostic potential in an enzyme linked immunosorbent assay. Clin. Diag. Lab. Immunology 11:211-215, 2004.

56. Dumler, J. S., and J. S. Bakken. Ehrlichial diseases of humans: emerging tick-borne infections. Clin. Infect. Dis. 20:1102-1110, 1995.

57. Brown, W. C., McGuire, T. C., Zhu, D., Lewin, H. A., Sosnow, J., Palmer, G. H. Highly conserved regions of the immunodominant major surface protein 2 of the genogroup II ehrlichial pathogen *Anaplasma marginale* are rich in naturally derived CD4+T lymphocyte epitopes that elicit strong responses. J. Immunol. 166:1114-1124, 2001.

58. Dattwyler, R. J., Volkman, D. J., Luft B. J., et al: seronegative Lyme disease -dissociation of specific T and B lymphocyte responses to *Borrelia burgdorferi*. N.Engl. J. Med. 319:1441, 1988.

59. Zoschke D., Skemp, A., Defosse, D., Lymphoproliferative responses to *Borrelia burgdorferi* in Lyme Disease. Ann Intern Med. 114:285, 1991.

60. Dressler, F., Yoshinar, N., Steere, A. The T-cell proliferative assay in the diagnosis of Lyme Disease. Ann Intern Med. 115:533, 1991.

61. Giambarolomei, G. H., V. A. Dennis, B. L. Lasater, and M. T. Philipp. 1999. Induction of pro and anti-inflammatory cytokines by *Borrelia burgdorferi* lipoproteins in monocytes is mediated by CD14. Infect. Immun. 67:140-147.

62. Giambartolomei, G. H., V. A. Dennis, and M. T. Philipp. 1998. *Borrelia burgdorferi* stimulates the production of interleukin-10 in peripheral blood mononuclear cells from unifected humans and rhesus monkeys. Infect. Immun. 66:2691-2697

63. Haupl, T., S., Landgraf, P. Netusil, N. Biller, C. Capiau, P. Desmons, P. Hauser, and G. R. Burmester. 1997. Activation of monocytes by three OspA vaccine candidates: lipoprotein OspA is a potent stimulator of monokines. FEMS Immunol. Med. Microbiol. 19:15-23.

64. Diterich, I., L. Harter, D. Hassler, A. Wendel, and T. Hartung. 2001. Modulation of cytokine release in ex vivo stimulated blood from borreliosis patients. Infect. Immun. 69:687-694.
65. Hirschfeld, M.,C. J. Kirschning, R. Schwandner, H. Wesche, J. H. Weis, R. M. Wooten, and J. J. Weis. 1999. Cutting edge:inflammatory signaling by *Borrelia burgdorferi* lipoproteins is mediated by toll like receptor 2. J. Immunol. 163:2382-2386.
66. Vojdani, A., Vojdani, E., Cooper, E. L. Antibodies to myelin basic protein, myelin oligodendrocytes peptides α-B-Crystallin, lymphocyte activation and cytokine production in patients with multiple sclerosis. J. Internal Medicine 254:363-374, 2003.
67. Giambartolomi, G. H., Dennis, V. A., Lasater, B. L. etal. Autocrine and exocrine regulation of interleukin- 10 production in THP- 1 cells stimulated with *Borrelia burgdorferi* lipoproteins. Infection and Immunity 70:1881-18

What is claimed is:

1. A method for determining the presence or possibility of a *Borrelia, Babesia*, and *Ehrlichia* infection in a patient, comprising the steps of:
   a) determining a level of antibodies against peptides of infective agents from each of *Borrelia, Babesia*, and *Ehrlichia*, wherein said *Borrelia* peptide has the sequence shown in SEQ ID NO: 7, said *Babesia* peptide has the sequence shown in SEQ ID NO: 12, and said *Ehrlichia* peptide has the sequence shown in SEQ ID NO: 15 in a sample from said patient;
   b) comparing the level of antibodies determined in step a) with levels of said antibodies from at least one healthy control individual, wherein
   (i) control levels of antibodies against *Borrelia, Babesia*, and *Ehrlichia* indicate that said patient does not have the presence or possibility of *Borrelia, Babesia*, and *Ehrlichia* infection;
   (ii) levels of antibodies greater than two standard deviations above control levels against said *Borrelia* peptide indicate a presence or possibility of an infection with *Borrelia;*
   (iii) greater than two standard deviations above control levels of antibodies against peptides of *Babesia* indicate a presence or possibility of an infection with *Babesia*; and
   (iv) greater than two standard deviations above control levels of antibodies against peptides of *Ehrlichia*, indicate a presence or possibility of an infection with *Ehrlichia*.

2. The method of claim 1, wherein the *Borrelia* is a species selected from the group consisting of *Borrelia burgdorferi sensu lato, B. garinii, B. sensu stricto*, and *B. afzelii*.

3. The method of claim 1, wherein step a) further comprises determining a level of antibodies against *Treponema*.

4. The method of claim 1, wherein the antibodies are selected from the group consisting of IgG, IgM, and IgA.

5. The method of claim 1, wherein the antibody levels are determined using an immunoassay.

6. The method of claim 1, wherein the antibodies in step a) and b) are measured from blood.

7. A kit for diagnosing exposure to *Babesia* and *Ehrlichia* infection in a patient comprising at least one peptide of infective agents from each of *Babesia* and *Ehrlichia*, wherein said *Babesia* peptide has the sequence shown in SEQ ID NO: 12, and said *Ehrlichia* peptide has the sequence shown in SEQ ID NO: 15.

8. The kit of claim 7, further comprising a *Borrelia* peptide having the sequence shown in SEQ ID NO: 7.

9. The kit of claim 7 further comprising standards, negative controls, positive controls, substrate, and an immunoassay selected from the group consisting of ELISA test, dot blot, and multi-peptide ELISA Blot.

10. The kit of claim 7 further comprising a component selected from the group consisting of nitrocellulose paper, plastics or combs, directions for preparation of specimens and serum diluents, wash buffers, and substrate buffers.

11. The method of claim 5, wherein the immunoassay is selected from the group consisting of an ELISA test, dot blot, and Multi-Peptide ELISA Blot.

* * * * *